United States Patent
Toyosada

(10) Patent No.: US 7,480,573 B2
(45) Date of Patent: Jan. 20, 2009

(54) FATIGUE CRACK GROWTH CURVE ESTIMATION METHOD, ESTIMATION PROGRAM, AND ESTIMATION DEVICE

(75) Inventor: Masahiro Toyosada, Fukuoka (JP)

(73) Assignee: Kyushu Tlo Company, Limited, Fukuoka (JP)

( * ) Notice: Subject to any disclaimer, the term of this patent is extended or adjusted under 35 U.S.C. 154(b) by 237 days.

(21) Appl. No.: 11/631,863

(22) PCT Filed: Jun. 30, 2005

(86) PCT No.: PCT/JP2005/012046

§ 371 (c)(1), (2), (4) Date: Jan. 8, 2007

(87) PCT Pub. No.: WO2006/006412

PCT Pub. Date: Jan. 19, 2006

(65) Prior Publication Data

US 2008/0052014 A1    Feb. 28, 2008

(30) Foreign Application Priority Data

Jul. 9, 2004    (JP)    ............... 2004-203938

(51) Int. Cl.
G01B 3/44    (2006.01)
(52) U.S. Cl. .......................................... 702/34
(58) Field of Classification Search .............. 702/34; 703/2, 6, 7; 73/804, 799
See application file for complete search history.

(56) References Cited

U.S. PATENT DOCUMENTS

| | | | | |
|---|---|---|---|---|
| 5,736,645 A * | 4/1998 | Chin-Chan et al. | ............ | 73/799 |
| 6,212,486 B1 * | 4/2001 | Huang et al. | ................... | 703/7 |
| 6,226,597 B1 * | 5/2001 | Eastman et al. | ............... | 702/34 |
| 6,301,970 B1 * | 10/2001 | Biggs et al. | ................... | 73/804 |
| 6,820,044 B2 * | 11/2004 | Groen et al. | ................... | 703/2 |
| 7,016,825 B1 * | 3/2006 | Tryon, III | ...................... | 703/6 |

OTHER PUBLICATIONS

Masahiro Toyosada et al., "*Fatigue Life Assessment for Welded Structures Without Initial Defects: An Algorithm for Predicting Fatigue Crack Growth From a Sound Site*", International Journal of Fatigue, vol. 26, No. 9, Available online Mar. 25, 2004, pp. 993-1002.

Masahiro Toyosada et al., "*Fatigue Crack Propagation for a Through Thickness Crack: A Crack Propagation Law Considering Cyclic Plasticity Near the Crack Tip*", International Journal of Fatigue, vol. 26, No. 9, Available Mar. 25, 2004, pp. 983-992.

(Continued)

Primary Examiner—Tung S Lau
Assistant Examiner—Xiuquin Sun
(74) Attorney, Agent, or Firm—Wenderoth, Lind & Ponack, L.L.P.

(57) ABSTRACT

There are provided a fatigue crack growth curve estimation method, an estimation program, and an estimation device capable of strictly estimating the detail of the metal fatigue end and the crack growth detail. The fatigue crack growth curve estimation device (1) uses a first calculation means (11), second calculation means (12), third calculation means (13), fourth calculation means (14), and fifth calculation means (15) to strictly estimate the detail of growth of a crack generated and growing in a first grain while omitting a calculation on the load pair not contributing to growth of the crack.

10 Claims, 8 Drawing Sheets

OTHER PUBLICATIONS

Masahiro Toyosada, "*Hiro Jumyo Suitei No Genjo To Kongo No Kadai*", Journal of the Japan Welding Society, vol. 72, No. 5, Jul. 5, 2003, pp. 424-435.

Toshio Niwa, Masahiro Toyosada, "*Kiretsu Kaiheiko Model Ni Okeru Kiretsu Seichoji No Sosei Shushuku Keisu Ni Kansuru Ichikosatsu*", Journal of the Society of Naval Architects of Japan, No. 188, 2000, pp. 669-678.

Masahiro Toyosada, Toshio Niwa, Junichi Sakai, "*Physical Meaning of $\Delta K_{RP}$ and Fatigue Crack Propagation in the Residual Stress Distribution Field*", International Journal of Fatigue, vol. 19, Supp. No. 1, 1997, pp. S161-S166.

Masahiro Toyosada, Toshio Niwa et al., "*$\Delta K_{RP}$ No Butsuriteki Imi To Kozobutsu No Hiro Jumyo Suiteiho*", Journal of the Society of Naval Architects of Japan, No. 180, 1996, pp. 539-547.

Masahiro Toyosada, Toshio Niwa, "*Algorithm of Fatigue Life Assessment by a Unified Theorem Without Distinguishing Between the Crack Initiation and the Propagation Life—Assessment of Fatigue Life for a Crack Emanating From a Notch—*", NK Tech Bulletin vol. 13, 1995, pp. 1 to 10.

Masahiro Toyosada, Toshio Niwa, "*Zanryu Oryokuba Ni Okeru Hiro Kiretsu Denpa Kyodo—RPG Kijun Ni Yoru Hiro Kiretsu Denpa Kyodo No Kenkyu (7th Report)*", Journal of the Society of Naval Architects of Japan, No. 178, 1995, pp. 505-511.

* cited by examiner

Numbers in circle represent linear rod element number

FATIGUE CRACK GROWTH CURVE ESTIMATION METHOD, ESTIMATION PROGRAM, AND ESTIMATION DEVICE

TECHNICAL FIELD

The present invention relates to an estimation method, an estimation program, and an estimation device for quantitatively estimating a fatigue crack initiation and growth curve at a stress concentrated area in a steel structure being a polycrystal.

BACKGROUND ART

With the development of industrial technology, demands for high efficiency, high performance, low cost, and safety have been further increased, and the usage environment of a steel structure has become severe. Thus, a design engineer is desired to rationally design a structure from mutually contradictory standpoints of high performance, economically efficiency, and safety.

However, there are often cases where a structure being supposed to be designed safely is damaged earlier than expected. In the case of a steel structure, it is said recently that "fatigue" directly or indirectly causes 80% or more of the damage as a result of dramatically improving the performance of a material.

Fatigue design is carried based on an S-N curve, in which break (crack initiation) life of a test piece under constant load amplitude is simply expressed as a function of stress amplitude, without considering an actual physical phenomenon, with only focusing attention on that cumulative stress frequency distribution applied on the structure comes to a certain fatigue damage level or less. Fatigue design using the S-N curve is effective to some extent as an empirical rule being feedback on actual use, but information about the size of a crack and the like cannot be obtained and there are many cases where the fatigue design using the S-N curve is disabled in a new style structure.

In damage analysis, on the other hand, there are many cases where crack propagation life assessment is carried out with postulating the existence of an initial crack based on the fracture mechanics. In this case, the supposed initial crack is appropriately adjusted so as to fit with damage, so that the fatigue design behaves as if it would function properly. In actual fact, however, the fatigue design only takes measures against individuals by reducing operating stress by increasing thickness and the like, and any fundamental treatment cannot be adopted. Therefore, it is desired to establish a fatigue design method by which the initiation and the propagation of a crack can be discussed on an equal footing.

The inventor has pointed out a contradiction that the fatigue design using the S-N curve assumes that a crack of a certain size suddenly appears in a sound area and a fatigue phenomenon belonging to the category of stable fracture is dealt as unstable fracture so far. As a result of study for a long period of time, the inventor found out that the initiation and the propagation of a crack could be assessed with a single parameter before anyone else in the world, and developed theory that a continuous crack growth curve could be assessed from a crack of a size zero by this parameter.

The inventor estimates fatigue life of a crack propagating through a first grain as described in Non-patent document 1 with assuming a case wherein a certain amplitude load is cyclically applied on the basis of the simple assumption that a tensile plastic zone appears during a loading process and a compressive plastic zone appears during an unloading process and the size of a region which both of the zones overlap determine crack propagation rate.

Non-patent document 1: "Fatigue Life Assessment For Steel Structures" written by Masahiro Toyosada and Toshio Niwa, published by Kyoritsu Shuppan Co., Ltd. on Dec. 25, 2001, pages 182 to 186

PROBLEMS TO BE SOLVED BY THE INVENTION

According to the method described in the foregoing Non-patent document 1, the inventor makes it possible to estimate a continuous crack growth curve from a crack with the size of zero. The method described in the foregoing Non-patent document 1, however, has the following problems in calculating the initial tip position of a fatigue damage accumulated region.

In a loading process on a long crack, it is assumed that the relation between a stress intensity factor range $\Delta K_{RP}$ corresponding to load amplitude in the section of growing a tensile plastic zone and the fatigue damage accumulated region still holds at a point of time when the crack reaches a first grain boundary at a notch root. The tip position of the fatigue damage accumulated region is calculated from $\Delta K_{RP}$ at the time of reaching the first grain boundary at a notch root.

The crack is a shear crack in a first stage and tensile stress is transmitted on a crack surface. In the long crack, however, the tensile stress is not transmitted to a crack surface, so that assumption described above does not always hold. Furthermore, the crack is the shear crack in the first stage and the tensile stress is transmitted on the crack surface, but the assumption totally ignores such a phenomenon.

In other words, irrespective of assuming a closing shear crack in estimating the fatigue crack growth curve, an opening crack is assumed in the stage of calculating parameters necessary for estimating the fatigue crack curve.

The method described in the foregoing Non-patent document 1 makes it possible to estimate the fatigue crack growth curve including crack growth inside the first grain, but the crack inside the first grain is the opening crack from the beginning from the viewpoint of safety because of including the assumption described above. The detailed behavior of a transition phenomenon in which the crack propagating through the first grain changes from the shear crack to the opening crack is not clear.

Considering the foregoing problems, an object of the present invention is to provide a method for estimating a fatigue crack growth curve, an estimation program, and an estimation device which can precisely estimate fatigue life of metal and the detailed behavior of the initiation and growth of a crack in accordance with a practical phenomenon in which the crack continuously grows in a sound area from a crack size of zero, in other words, from a condition in which there is no crack at all.

MEANS FOR SOLVING THE PROBLEMS

According to the present invention, a method for estimating a fatigue crack growth curve from a sound area using equivalent distributed stress which reproduces a relation between a crack length and a stress intensity factor in an actual structure by external force and internal force due to residual stress into a straight crack in an infinitely wide plate. The method includes: a first step of calculating a tip position of a tensile plastic zone and an inherent displacement which forms a tensile residual deformation layer at a maximum load during cyclic loading on a stress concentrated area; a second step of calculating the inherent displacement at a minimum load, and calculating a tip position of a compressive plastic zone from the inherent displacement; a third step of calculating a fatigue damage accumulated region formed ahead of the crack from the tip position of the tensile plastic zone and the tip position of the compressive plastic zone, and calculating an increment of the crack from the fatigue damage accumulated region in order to add the increment of the crack to the crack length; a fourth step of setting, when the crack length from the sound area is smaller than a first grain size at a notch root, an increment of plastic strain to "0", the plastic strain being formed by a pair of the maximum load and the minimum load in applying the cyclic load inside the grain only in the compressive plastic zone in a load cycle in which the tensile plastic zone at the maximum load is larger than the compressive plastic zone at the minimum load, or only in the tensile plastic zone in a load cycle in which the tensile plastic zone at the maximum load is smaller than the compressive plastic zone at the minimum load, then calculating an increment of plastic strain outside of the grain to calculate cumulative plastic strain from the increment of plastic strain, and, when the crack length from the sound area is equal to or larger than the first grain size at the notch root, calculating the increment of plastic strain and calculating the cumulative plastic strain from the increment of plastic strain, and, when the cumulative plastic strain inside the grain reaches a ductility limit specific to a material composing the stress concentrated area, judging the crack to have changed into an opening mode crack, and calculating inherent displacement taken in a crack incremental region; and a fifth step of calculating a yield stress under the next cyclic load at the next maximum load, and returning the process to the first step.

The fatigue damage accumulated region formed ahead of the crack refers to a region in which the tensile plastic zone determined by the tip position of the tensile plastic zone and the compressive plastic zone determined by the tip position of the compressive plastic zone overlap one another. The crack incremental region refers to a region in which the crack propagates by the crack increment.

According to the present invention, since it is assume that the size of the fatigue damage accumulated region being the cyclic plastic zone controls the crack propagation rate, it is possible to precisely estimate fatigue life of metal and the detailed behavior of the initiation and growth of the crack in accordance with a practical phenomenon in which the crack continuously grows from a sound area without the crack at all.

Threshold values such as a lower limit $\Delta K_{th}$ of fatigue crack propagation obtained under amplitude with small load variation are generally assumed to be maintained constant under any load variation as desired irrespective of the absence of a guarantee that the threshold values are kept constant under a random load because there is no other way. According to the present invention, however, it is assumed that the size of the fatigue damage accumulated region controls the crack propagation rate. Using the size of the fatigue damage accumulated region enables physically clear management by which if the fatigue damage accumulated region does not occur, in other words, if plastic strain does not proceed, the crack does not propagate.

Inside the first grain at the notch root, the crack is the shear crack on which not only compressive stress but also tensile stress is transmitted at first. After the shear crack exceeds the first grain boundary, dislocation shifts to a direction inclined from a slipband inside the first grain, so that plastic strain is accumulated in a direction perpendicular to a slip by the cyclic load inside the first grain. It is assumed that the position where this accumulated plastic strain reaches the ductility limit specific to the material is changed into the opening mode crack on which the tensile stress is not transmitted, so that it is possible to reproduce a practical behavior in which the shear crack is gradually changed into the opening mode crack. It may be assumed that the shear mode crack is changed into the opening mode crack by Miner law using Manson-Coffin law instead of the cumulative plastic strain. Also in this case, it is possible to reproduce a practical behavior in which the shear crack is gradually changed into the opening crack.

The inherent displacement formed ahead of the crack differs according to a load level, and the inherent displacement taken at a load level of generating the crack differs too. Thus, it is possible to analytically give the same load as the re-tensile plastic zone's generated load obtained by experiments by comparing the multiple of the difference between crack opening displacement at the minimum load and crack opening displacement in a case where contact stress is not applied because a crack closing zone does not occur by a ratio determined as a function of the cumulative plastic strain with the crack opening displacement at the minimum load.

It is necessary to calculate a region in which dislocations are activated at the first maximum load, and hence a tensile yield region is calculated on the basis of a yield stress under the cyclic load. However, the dislocation actually starts shifting at a proportional limit. It is quite difficult, however, to precisely calculate the proportional limit, so that in the present invention the yield stress under the cyclic load is used instead of the proportional limit and yield stress is increased until a static yield stress by work hardening with the propagation of the crack. Accordingly, it is guaranteed that plastic grows in a second cycle or later in an initial state in which the crack propagates in a shearing manner under constant load amplitude. At the same time, when load amplitude which is slightly larger than a fatigue limit is applied in a state where the crack stops to grow by passing many cycles immediately below a fatigue limit, the present invention realizes the so-called coaxing effect, by which the fatigue limit is apparently increased without propagating the crack.

A method of the present invention for estimating a fatigue crack growth curve from a sound area using equivalent distributed stress which reproduces a relation between a crack length and a stress intensity factor in an actual structure by external force and internal force due to residual stress into a straight crack in an infinitely wide plate. The method includes: a first step of setting an initial value of the crack length to "0", and setting an initial value of a crack mode index to "1", which represents a shear mode crack and an opening mode crack by "1" or "0" and then calculating, when a cyclic load is applied on a stress concentrated area, an inherent displacement which forms a tensile residual deformation layer at a maximum load from a tip position of a tensile plastic zone which is calculated from vertical equivalent distributed stress applied on an arbitrary x axis at the maximum load, vertical equivalent distributed stress in the x axis caused by a static load, equivalent distributed stress corresponding to residual stress applied on the x axis, and a yield stress and a plastic constraint factor under the cyclic load; a second step of calculating the inherent displacement at a minimum load from the vertical equivalent distributed stress applied on the x axis in the case of applying the minimum load and a unit external load of the cyclic load, the vertical equivalent distributed stress in the x axis caused by the static load, the equivalent distributed stress corresponding to the residual stress applied on the x axis, and the inherent displacement at the maximum load, and then calculating a tip position of a compressive plastic zone at the minimum load from inherent displacement at the maximum load and the inherent displacement at the minimum load, and calculating the inherent displacement in a compressive yield zone from inherent displacement at the minimum load and the yield stress and the plastic constraint factor under the cyclic load; a third step of calculating a fatigue damage accumulated region formed ahead of the crack from the tip position of the tensile plastic zone and the tip position of the compressive plastic zone, and calculating an increment of the crack from the fatigue damage accumulated region in order to add the increment of the crack to the crack length; a fourth step of setting, when the crack length from the sound area is smaller than a first grain size at a notch root, an increment of plastic strain to "0", the plastic strain being formed by a pair of the maximum load and the minimum load in applying the cyclic load inside the grain only in the compressive plastic zone in a load cycle in which the tensile plastic zone at the maximum load is larger than the compressive plastic zone at the minimum load, or only in the tensile plastic zone in a load cycle in which the tensile plastic zone at the maximum load is smaller than the compressive plastic zone at the minimum load, then calculating an increment of plastic strain outside of the grain from the variation of the thickness of the inherent displacement to calculate cumulative plastic strain from the increment of plastic strain, and, when the crack length from the sound area is equal to or larger than the first grain size at the notch root, calculating the increment of plastic strain from the variation of the inherent displacement, and calculating the cumulative plastic strain from the increment of plastic strain, and, when the cumulative plastic strain inside the grain reaches a ductility limit specific to a material composing the stress concentrated area, judging the crack to have changed into an opening mode crack, and setting the crack mode index to "0", and calculating the inherent displacement taken in a crack incremental region and the yield stress and the plastic constraint factor under the cyclic load; and a fifth step of calculating a yield stress under the next cyclic load at the next maximum load from the vertical equivalent distributed stress applied on the arbitrary x axis at the next maximum load, the vertical equivalent distributed stress in the x axis caused by the static load, the equivalent distributed stress corresponding to the residual stress applied on the x axis, and the plastic constraint factor, and returning the process to the first step.

According to the present invention, it is possible to calculate the growth of the fatigue crack on the basis of the size of the fatigue damage accumulated region being a cyclic plastic zone caused by the pair of the maximum load and the minimum load. Thus, it is possible to precisely estimate fatigue life of metal and the detailed behavior of the initiation and growth of the crack in accordance with a practical phenomenon in which the crack continuously grows from a state without the crack at all with considering a load history applied on the crack.

An estimation program of a fatigue crack growth curve according to the present invention for making a computer, which sets an initial crack length to "0" and sets an initial value of a crack mode index to "1" which represents a shear mode crack and an opening mode crack by "1" or "0" and stores them on memory means, carry out: a first step of calculating, when a cyclic load is applied on a stress concentrated area, an inherent displacement which forms a tensile residual deformation layer at a maximum load from a tip position of a tensile plastic zone which is calculated from vertical equivalent distributed stress applied on an arbitrary x axis at the maximum load, vertical equivalent distributed stress in the x axis caused by a static load, equivalent distributed stress corresponding to residual stress applied on the x axis, and a yield stress and a plastic constraint factor under the cyclic load, and storing the tip position of the tensile plastic zone and the inherent displacement in the memory means; a second step of calculating the inherent displacement at a minimum load from the vertical equivalent distributed stress applied on the x axis in the case of applying the minimum load and a unit external load of the cyclic load, the vertical equivalent distributed stress in the x axis caused by the static load, the equivalent distributed stress corresponding to the residual stress applied on the x axis, and the inherent displacement at the maximum load read from the memory means, and then calculating a tip position of a compressive plastic zone at the minimum load from inherent displacement at the maximum load read from the memory means and the inherent displacement at the minimum load, and calculating the inherent displacement in a compressive yield zone from inherent displacement at the minimum load and the yield stress and the plastic constraint factor under the cyclic load, and storing the inherent displacement and the tip position of the compressive plastic zone in the memory means; a third step of calculating a fatigue damage accumulated region formed ahead of the crack from the tip position of the tensile plastic zone and the tip position of the compressive plastic zone which are read from the memory means, and calculating an increment of the crack from the fatigue damage accumulated region in order to add the increment of the crack to the crack length and store a result in the memory means; a fourth step of setting, when the crack length from the sound area is smaller than a first grain size at a notch root, an increment of plastic strain to "0", the plastic strain being formed by a pair of the maximum load and the minimum load in applying the cyclic load inside the grain only in the compressive plastic zone in a load cycle in which the tensile plastic zone at the maximum load is larger than the compressive plastic zone at the minimum load, or only in the tensile plastic zone in a load cycle in which the tensile plastic zone at the maximum load is smaller than the compressive plastic zone at the minimum load, then calculating an increment of plastic strain outside of the grain from the variation of the thickness of the inherent displacement read from the memory means in order to calculate cumulative plastic strain from the increment of plastic strain and store it in the memory means, and, when the crack length from the sound area is equal to or larger than the first grain size at the notch root, calculating the increment of plastic strain from the variation of the inherent displacement read from the memory means, and calculating the cumulative plastic strain from the increment of plastic strain to store it in the memory means, and, when the cumulative plastic strain inside the grain reaches a ductility limit specific to a material composing the stress concentrated area, judging the crack to have changed into an opening mode crack, and setting the crack mode index to "0" to store it in the memory means, and calculating the inherent displacement taken in a crack incremental region and the yield stress and the plastic constraint factor under the cyclic load to store it in the memory means; and a fifth step of calculating a yield stress under the next cyclic load at the next maximum load from the vertical equivalent distributed stress applied on the arbitrary x axis at the next maximum load, the vertical equivalent distributed stress in the x axis caused by the static load, the equivalent distributed stress corresponding to the residual stress applied on the x axis, the plastic constraint factor, and the crack mode index read from the memory means, and storing it in the memory means, and then returning the process to the first step. Running the estimation program of the fatigue crack growth curve according to the present invention makes it possible to carry out the foregoing method for estimating the fatigue crack growth curve according to the present invention.

An estimation device of a fatigue crack growth curve according to the present invention includes: memory means for storing an initial value of a crack length set to "0" and an initial value of a crack mode index to "1", which represents a shear mode crack and an opening mode crack by "1" or "0"; first operation means for calculating, when a cyclic load is applied on a stress concentrated area, an inherent displacement which forms a tensile residual deformation layer at a maximum load from a tip position of a tensile plastic zone which is calculated from vertical equivalent distributed stress applied on an arbitrary x axis at the maximum load, vertical equivalent distributed stress in the x axis caused by a static load, equivalent distributed stress corresponding to residual stress applied on the x axis, and a yield stress and a plastic constraint factor under the cyclic load, and storing the tip position of the tensile plastic zone and the inherent displacement in the memory means; second operation means for calculating the inherent displacement at a minimum load from the vertical equivalent distributed stress applied on the x axis in the case of applying the minimum load and a unit external load of the cyclic load, the vertical equivalent distributed stress in the x axis caused by the static load, the equivalent distributed stress corresponding to the residual stress applied on the x axis, and the inherent displacement at the maximum load read from the memory means, and then calculating a tip position of a compressive plastic zone at the minimum load from the inherent displacement at the maximum load read from the memory means and the inherent displacement at the minimum load, and calculating the inherent displacement in a compressive yield zone from inherent displacement at the minimum load and the yield stress and the plastic constraint factor under the cyclic load, and storing the inherent displacement and the tip position of the compressive plastic zone in the memory means; third operation means for calculating a fatigue damage accumulated region formed ahead of the crack from the tip position of the tensile plastic zone and the tip position of the compressive plastic zone which are read from the memory means, and calculating an increment of the crack from the fatigue damage accumulated region in order to add the increment of the crack to the crack length and store a result in the memory means; fourth operation means for setting, when the crack length from the sound area is smaller than a first grain size at a notch root, an increment of plastic strain to "0", the plastic strain being formed by a pair of the maximum load and the minimum load in applying the cyclic load inside the grain only in the compressive plastic zone in a load cycle in which the tensile plastic zone at the maximum load is larger than the compressive plastic zone at the minimum load, or only in the tensile plastic zone in a load cycle in which the tensile plastic zone at the maximum load is smaller than the compressive plastic zone at the minimum load, then calculating an increment of plastic strain outside of the grain from the variation of the inherent displacement read from the memory means in order to calculate cumulative plastic strain from the increment of plastic strain and store it in the memory means, and, when the crack length from the sound area is equal to or larger than the first grain size at the notch root, calculating the increment of plastic strain from the variation of the inherent displacement read from the memory means, and calculating the cumulative plastic strain from the increment of plastic strain to store it in the memory means, and, when the cumulative plastic strain inside the grain reaches a ductility limit specific to a material composing the stress concentrated area, judging the crack mode to have changed into an opening mode crack, and setting the crack mode index to "0" to store it in the memory means, and calculating the inherent displacement taken in a crack incremental region outside of the grain from the cumulative plastic strain and the yield stress and the plastic constraint factor under the cyclic load to store it in the memory means; and fifth operation means for calculating a yield stress under the next cyclic load at the next maximum load from the vertical equivalent distributed stress applied on the arbitrary x axis at the next maximum load, the vertical equivalent distributed stress in the x axis caused by the static load, the equivalent distributed stress corresponding to the residual stress applied on the x axis, the plastic constraint factor, and the crack mode index read from the memory means, and storing it in the memory means, and then returning the process to the first operation means. The estimation device of the fatigue crack growth curve according to the present invention can carry out the foregoing method for estimating the fatigue crack growth curve according to the present invention.

In the method for estimating the fatigue crack growth curve according to the present invention, it is preferable that, when a constant amplitude load is repeatedly and continuously applied on the stress concentrated area, in the third step, the fatigue damage accumulated region is calculated, the fatigue damage accumulated region provides an increment of the crack which can propagate at a time, and the number of cycles necessary for the increment of the crack is calculated from a crack propagation equation, and in the fourth step, when the crack length from the sound area is smaller than the first grain size at the notch root, the increment of plastic strain is set to "0," outside of the grain, the increment of plastic strain is calculated from the variation of the inherent displacement, and the cumulative plastic strain is calculated by multiplying the increment of plastic strain by the number of cycles, and, when the crack length from the sound area is equal to or larger than the first grain size at the notch root, the increment of plastic strain is calculated from the variation of the inherent displacement, and the cumulative plastic strain is calculated by multiplying the increment of plastic strain by the number of cycles, and inside the grain, when the cumulative plastic strain reaches the ductility limit specific to the material composing the stress concentrated area, the crack mode is judged to have changed into the opening mode crack, and the crack mode index is set to "0", and outside of the grain, the inherent displacement taken in the crack incremental region is calculated from the cumulative plastic strain and the yield stress and the plastic constraint factor under the cyclic load.

According to the present invention, when the constant amplitude load continues for a while, the crack can be grown at a time with considering that an upper limit for the increment of the crack which can advance at a time by calculation is 5% of the size of the fatigue damage accumulated region.

Furthermore, it is desirable that the method for estimating the fatigue crack growth curve according to the present invention include a load extraction step for extracting only a load pair of a maximum load and a minimum load contributing to crack growth. The load extraction step makes it possible to omit calculation about the crack growth with respect to a load pair which does not contribute to the crack growth.

In the load extraction step according to the method for estimating the fatigue crack growth curve of the present invention, it is desirable that the load pair of the maximum load and the minimum load contributing to the crack growth be extracted with the use of a re-compressive plastic zone's generated load calculated from the inherent displacement, the vertically equivalent distributed stress applied on the x axis when a unit load is applied, the vertical equivalent distributed stress in the x axis caused by the static load, the equivalent distributed stress corresponding to the residual stress applied on the x axis, the yield stress under the cyclic load, and the plastic constraint factor at the maximum load in an unloading process in continuously applying the cyclic load on the stress concentrated area, and a re-tensile plastic zone's generated load calculated from the inherent displacement, the vertically equivalent distributed stress when a unit external load is applied, the vertical equivalent distributed stress in the x axis caused by the static load, the equivalent distributed stress corresponding to the residual stress applied on the x axis, the yield stress under the cyclic load, and the plastic constraint factor at the minimum load in a loading process in continuously applying the cyclic load on the stress concentrated area, as threshold values.

In the load range between the maximum load and the re-compressive plastic zone's generated load in the unloading process and in the load range between the minimum load and the re-tensile plastic zone's generated load in the loading process, only elastic deformation appears and hence a plastic region does not occur. Thus, using the re-compressive plastic zone's generated load and the re-tensile plastic zone's generated load as threshold values makes it possible to extract load fluctuation directly contributing to the propagation of the crack, and can provide a load calculation method which is apparently superior to an indirect waveform calculation method such as a rain flow method and a range pair method.

ADVANTAGEOUS EFFECT OF THE INVENTION (1) According to the present invention, assuming that the size of a fatigue damage accumulated region being a cyclic plastic zone determines crack propagation rate, it is possible to precisely estimate fatigue life of metal and the detailed behavior of the initiation and growth of a crack in accordance with a practical phenomenon in which the crack continuously grows in a sound area without the crack at all.

(2) According to the present invention, assuming that the size of the fatigue damage accumulated region determines the crack propagation rate and using the fatigue damage accumulated region enables physically clear management by which if the fatigue damage accumulated region does not occur, in other words, if plastic strain does not proceed, the crack does not propagate.

(3) According to the present invention, inside of a first grain at a notch root, the crack is a shear crack at first on which not only compressive stress but also tensile stress is transmitted. After the shear crack exceeds a first grain boundary, dislocation shifts to a direction inclined from a slipband inside the first grain, so that plastic strain is accumulated in a direction perpendicular to a slip by a cyclic load inside the first grain. It is assumed that a position where this accumulated plastic strain reaches a ductility limit specific to a material is changed into an opening mode crack on which the tensile stress is not transmitted, so that it is possible to reproduce a practical behavior in which the shear crack is gradually changed into the opening crack.

(4) According to the present invention, the inherent displacement formed ahead of the crack differs according to a load level, and the inherent displacement taken at a load level of generating the crack differs too. Thus, it is possible to analytically give the same load as the re-tensile plastic zone's generated load obtained by experiments by comparing the multiple of the difference between crack opening displacement at the minimum load and crack opening displacement in a case where contact stress is not applied because a crack closing zone does not occur by a ratio determined as a function of the cumulative plastic strain with the crack opening displacement at the minimum load.

(5) According to the present invention, it is guaranteed that plastic grows in a second cycle or later too in an initial state in which the crack propagates in a shearing manner under constant load amplitude. At the same time, when load amplitude which is slightly larger than a fatigue limit is applied in a state that the crack stops to grow by passing many cycles immediately below a fatigue limit, the so-called coaxing effect by which the fatigue limit is apparently increased without propagating the crack is realized.

(6) It is possible to grow the crack at a time with considering that an upper limit for an increment of the crack which can advance at a time by calculation is 5% when a constant amplitude load continues for a while.

(7) According to the present invention, in the load range between the maximum load and the re-compressive plastic zone's generated load in an unloading process and in the load range between the minimum load and the re-tensile plastic zone's generated load in a loading process, only elastic strain appears and a plastic region does not occur. Thus, using the re-compressive plastic zone's generated load and the re-tensile plastic zone's generated load as threshold values makes it possible to extract load fluctuation which directly contributes to the propagation of the crack.

DESCRIPTION OF NUMERALS

Figure 1:
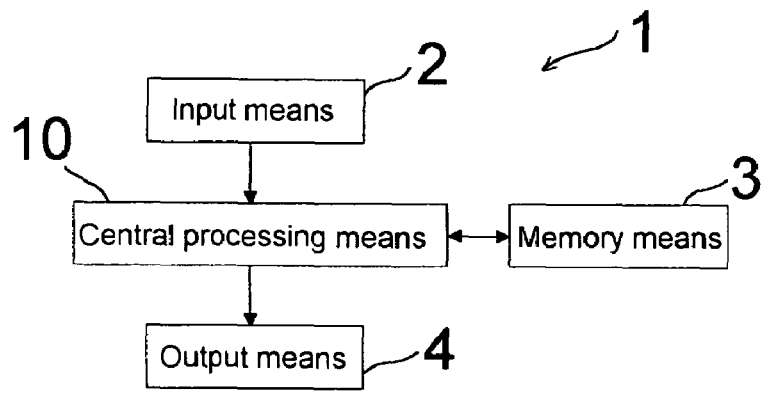
FIG. 1 is a diagram showing an estimation device of a fatigue crack growth curve according to a first embodiment of the present invention.

1 Estimation device of a fatigue crack growth curve
2 Input means
3 Memory means 4 Output means
5 Central processing means
11 First operation means
12 Second operation means
13 Third operation means
14 Fourth operation means
15 Fifth operation means

BEST MODE FOR CARRYING OUT THE INVENTION

First Embodiment

FIG. 1 shows an estimation device of a fatigue crack growth curve according to a first embodiment of the present invention.

The estimation device 1 of the fatigue crack growth curve includes input means 2, memory means 3, output means 4, and central processing means 10. The input means 2 is provided with, for example, a keyboard, a pointing device, or the like to input initial values of parameters necessary for operation. The input means 2 may read a file on which the initial values of the parameters necessary for operation are written to input them. The central processing means 10 includes a central processing unit of a computer or the like to carry out operation.

The memory means 3 temporarily stores values of parameters operated by the central processing means 10 on, for example, a hard disk, a memory of the computer, or the like. The output means 4 outputs the values of the parameters operated by the central processing means 10 to a recording medium. The output means 4 records electronic data on the recording medium such as, for example, a flexible disk, a hard disk, and a CD-ROM. The output means 4 may output data to a recording medium such as paper and a sheet through an image forming device.

Figure 2:
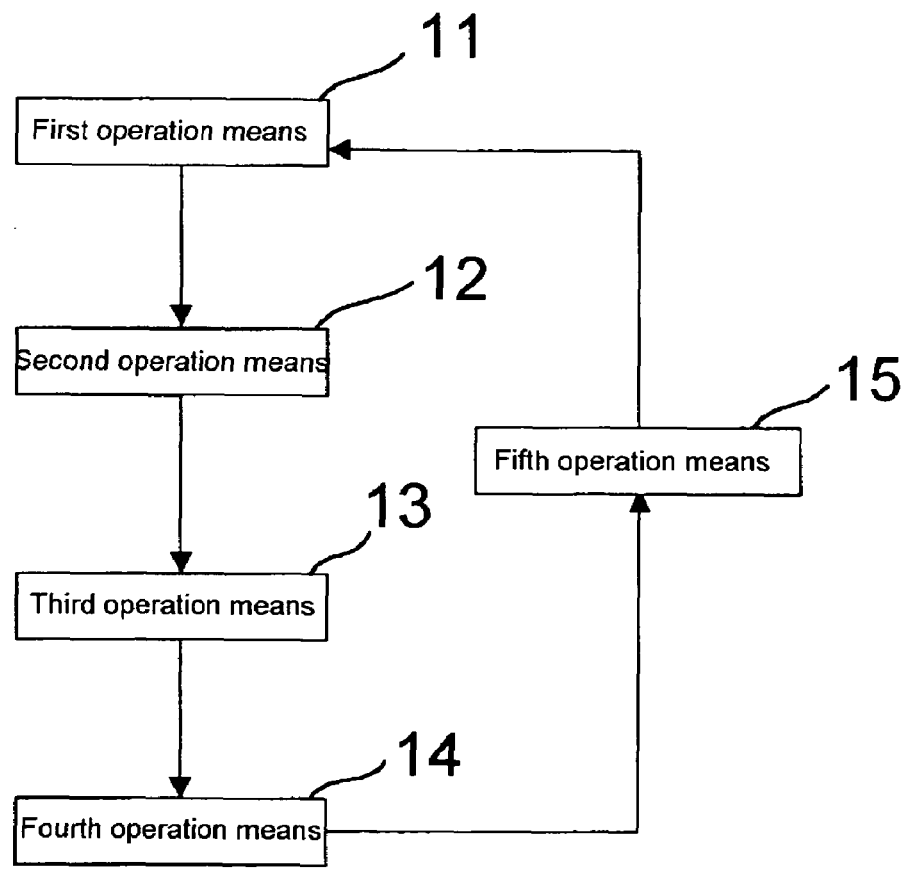
FIG. 2 is a functional block diagram of the estimation device of the fatigue crack growth curve according to the first embodiment of the present invention.

FIG. 2 is a functional block diagram of the central processing means 10 of FIG. 1.

As shown in FIG. 2, the central processing means 10 has first operation means 11, second operation means 12, third operation means 13, fourth operation means 14, and fifth operation means 15.

The details of the foregoing respective means 11 to 15 will be hereinafter described.

The first operation means 11 calculates the tip position of a tensile plastic zone at a maximum load, and calculates the inherent displacement at the maximum load from the tip position of the tensile plastic zone. Then, the first operation means 11 stores the tip position of the tensile plastic zone and the inherent displacement at the maximum load on the memory means 3.

The second operation means 12 calculates the inherent displacement at a minimum load from the inherent displacement at the maximum load read from the memory means 3, and calculates the tip position of a compressive plastic zone at the minimum load from the distribution of the inherent displacement at the maximum load and the minimum load. Then, the second operation means 12 calculates the inherent displacement in a compressive yield zone from a yield stress at that time, and stores the inherent displacement and the tip position of the compressive plastic zone on the memory means 3.

The third operation means 13 calculates a fatigue damage accumulated region formed ahead of a crack from the tip position of the tensile plastic zone and the tip position of the compressive plastic zone read from the memory means 3, and calculates an increment of the crack from the fatigue damage accumulated region. The third operation means 13 adds this increment of the crack to a crack length, and stores the crack length on the memory means 3.

The fourth operation means 14 sets an increment of plastic strain inside a grain to "0" when the crack length in a sound area read from the memory means 3 is smaller than the first grain size at a notch root. Outside of the grain, the fourth operation means 14 also calculates an increment of plastic strain from variation of the inherent displacement read from the memory means 3, and calculates cumulative plastic strain from the increment of plastic strain and stores it on the memory means 3. Furthermore, when the crack length in the sound area read from the memory means 3 is equal to or larger than the first grain size at the notch root, the fourth operation means 14 calculates an increment of plastic strain from variation of the inherent displacement read from the memory means 3, and calculates cumulative plastic strain from the increment of plastic strain and stores it on the memory means 3. Inside the first grain from the sound area, when the cumulative plastic strain read from the memory means 3 reaches a ductility limit specific to a material, the fourth operation means 14 sets a crack mode index at that position to "0" and stores it on the memory means 3. Outside of the grain, the fourth operation means 14 calculates the inherent displacement taken in a crack incremental region from the cumulative plastic strain and stores it on the memory means 3.

The fifth operation means 15 calculates a yield stress under the next cyclic load at the next maximum load from the crack mode index and equivalent stress distribution, and stores the yield stress on the memory means 3. Then, the processing returns to the first operation means 11.

Figure 3:
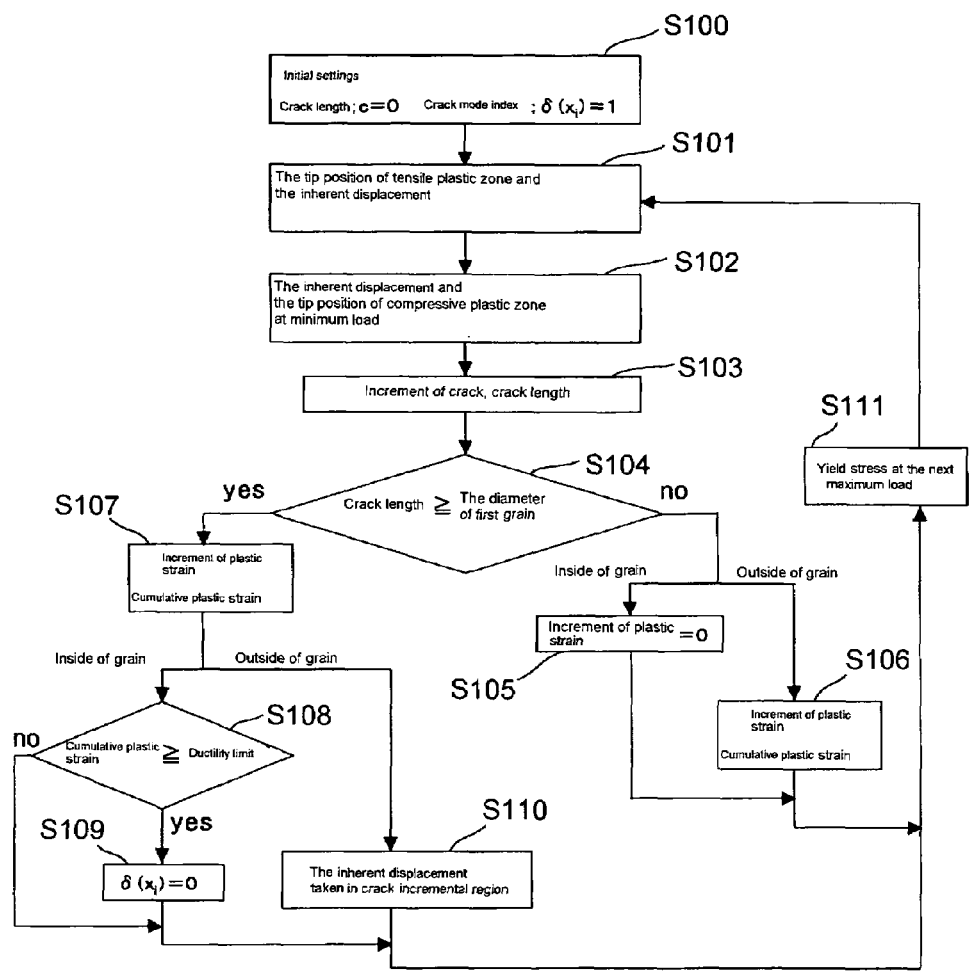
FIG. 3 is a diagram showing the details of processing of the estimation device of the fatigue crack growth curve according to the first embodiment of the present invention.

FIG. 3 is a flow chart showing the details of the processing of the central processing means 10 of FIG. 1. A method for estimating a fatigue crack growth curve according to the first embodiment of the present invention will be described on the basis of FIG. 3.

In the method for estimating the fatigue crack growth curve according to the first embodiment of the present invention, an initial crack is set at zero, in other words, the curve starts from a state in which a crack does not exist at all. Thus, a crack length c=0 at initial settings. If a crack appears in a first grain (the grain size=d) at the notch root, the crack does not suddenly become an opening crack but becomes a shear crack. Thus, using the crack mode index $\delta(x_i)$ representing a shear crack on which tensile stress is transmitted by "1" and represents an opening crack on which the tensile stress is not transmitted by "0," the crack mode index $\delta(x_i)=1$ as the initial settings (step S100). In this instance, $\delta(x_i)$ is defined only within the confines of $x_i \leq d$.

It is possible that the shear mode crack is assumed to change into the opening mode crack based on a Manson-Coffin law. In this case, the following equation holds.

$$D = \sum \left( \frac{|\Delta \varepsilon_{pi}|}{\varepsilon_f} \right)^2 \qquad \text{[Equation 1]}$$

wherein, $\varepsilon_f$ represents break ductility and $\Delta\varepsilon_{pi}$ represents an increment of plastic strain by a load pair in the i-th cycle. When a fatigue damage level D becomes "1," the shear mode crack may change into the opening mode crack, in other words, $\delta(x_i)$ changes into zero.

First, the tip position of the tensile plastic zone and the inherent displacement at the maximum load are calculated (step S101). Next, the inherent displacement, the tip position of the compressive plastic zone, and the inherent displacement in the compressive yield zone at the minimum load are calculated (step S102).

Furthermore, the fatigue damage accumulated region formed ahead of the crack is calculated. The increment of the crack is calculated from the fatigue damage accumulated region, and the increment of the crack is added to the crack length (step S103). Then, it is judged whether or not the crack length calculated in the step S103 reaches the first grain size (step S104). If the crack reaches the first grain boundary, the processing proceeds to a step S107. If not, the processing proceeds to steps S105 and S106.

When it is judged whether or not the crack reaches the first grain boundary in the step S104, a half of the diameter of the first grain may be a threshold value.

Setting a half of the diameter of the first grain as the threshold value means that it is assumed that a crack opening mode gradually starts appearing after the crack propagates to a position corresponding to a half of the diameter of the first grain. This is because when the grains closely arranged without space in three dimensions are cut in the bottom of the notch being a stress concentrated area, the distance between a boundary of the grain positioned in the bottom of the notch and the bottom of the notch is a half of the diameter of the grain on average, and it is assumed that a yield phenomenon starts occurring when the crack yields to a position a half of the diameter of the grain away in a calculation idealized in two dimensions.

A case where a half of the diameter of the first grain is set as the threshold value will be hereinafter described in judging whether or not the crack reaches the first grain boundary.

The increment of plastic strain inside of the first grain is set to "0" in the step S105. In the step S106, the increment of plastic strain outside of the first grain is calculated, and the cumulative plastic strain is calculated from the increment of plastic strain. After the steps S105 and S106 are completed, the processing proceeds to a step S111.

In the step S107, the increment of plastic strain is calculated, and the cumulative plastic strain is calculated from the increment of plastic strain. Next, in the first grain, whether or not the cumulative plastic strain reaches a ductility limit specific to a material composing the stress concentrated area is judged (step S108). If the cumulative plastic strain reaches the ductility limit specific to the material, a crack in that position is judged to have become the opening mode crack and the crack mode index $\delta(x_i)=0$ (step S109), and then the processing proceeds to the step S111. If the cumulative plastic strain does not reach the ductility limit, the processing proceeds to the step S111 as is. Outside of the first grain, the inherent displacement taken in the crack increment region is calculated (step S110), and operation goes to the step S111.

In the step S111, the yield stress under the cyclic load at the next maximum load is calculated. Then, the processing proceeds to the step S101.

Next, the details of calculation in each step will be described. After the initial settings are made in the step S100, the first operation means 11 calculates the tip position of the tensile plastic zone and the inherent displacement at the maximum load (step S101).

The stress intensity factor K value of a crack (with a crack length of a) in an actual structure is represented by $K=pg(x, a)$, when a pair of concentrated loads p is applied on a vertical crack surface in a position of x. The following equation holds under equivalent distributed stress by which the relation between external force and internal force due to residual stress and the stress intensity factor is reproduced into a crack in a single dimension.

[Equation 2]

$$\int_0^a \{P_{max}S(x) + s_m(x) + s_R(x)\}g(x, a)dx - \lambda\sigma_{CY}\int_0^a g(x, a)dx = 0 \quad (1)$$

wherein, $P_{max}$: maximum load, $S(x)$: vertical equivalent distributed stress when a unit external load is applied, $s_m(x)$: vertical equivalent distributed stress by a static load, $s_R(x)$: equivalent distributed stress corresponding to residual stress, $\sigma_{CY}$: a yield stress under a cyclic load, and $\lambda$: a plastic constraint factor. $pg(x, a)$ is the stress intensity factor K value when an unit bi-concentrated load is vertically applied on a crack surface an equal distance x away from the center of a linear thickness penetration crack (the whole length of the crack is 2a) to right and left in an infinite plate, and $g(x,a)$ is expressed as follows.

[Equation 3]

$$g(x, a) = \frac{2}{\sqrt{\pi a}}\frac{1}{\sqrt{1-(x/a)^2}} \quad (2)$$

wherein, x represents a distance from the notch root when the shear crack is projected on a main crack surface. Since the equivalent distributed stress is used, it is assured that elastic stress distribution ahead of the crack at the time when the crack becomes each size is the same as that ahead of the crack (for example, the deepest point of a surface crack) to be evaluated.

$P_{bmax}$ (0 at first) refers to a maximum load in the past. $P_{cmax}$ refers to a maximum load at present. When it is evaluated that a yield stress by an equation (28) described later is a static yield stress or more, the yield stress becomes the static yield stress and the tensile plastic zone grows beyond the tip position of the tensile plastic zone in the past.

Figure 4:
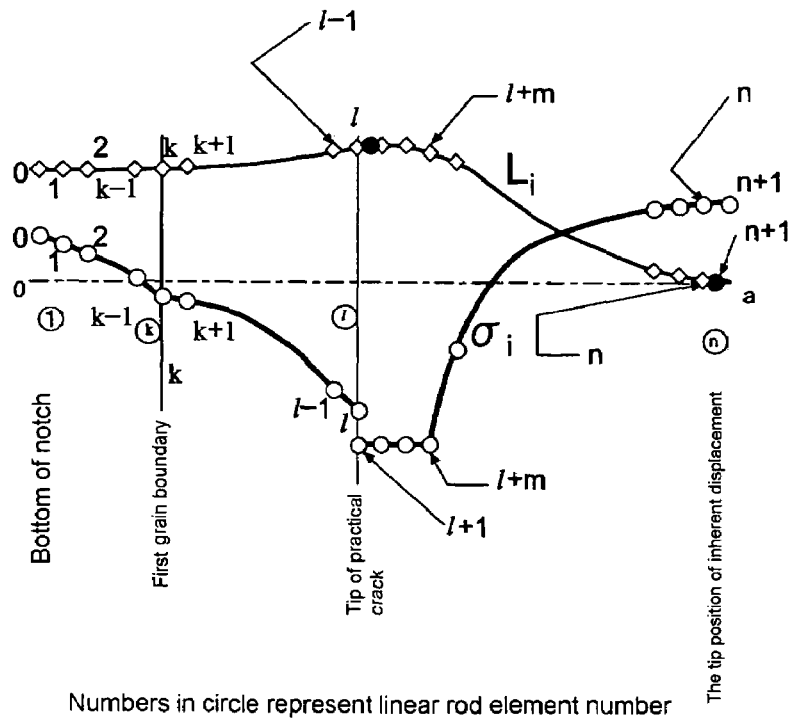
FIG. 4 is a drawing in which a length from a notch root to the tip position of a tensile plastic zone is divided into n.

FIG. 4 is a drawing in which a distance from the notch root to the tip position of the tensile plastic zone is divided into n. As shown in FIG. 4, a distance from 0 to a is divided into n. $S_i$ represents a value of $S(x)$ in a divided point $x_i$, and $s_{mRi}$ (i=0,n) represents a value of $s_{mR}(x)$ which is the sum total of $s_{mR}(x)$ and $s_R(X)$. $S(x)$ between the divided points and $s_{mR}(x)$ are assumed to linearly vary and a first-order theory is used. Substituting the equation (2) into the equation (1), equation (4) is obtained.

[Equation 4]

$$P_{cmax}\sum_{i=1}^{n}\left\{\frac{S_{i-1} - S_i}{x_{i-1} - x_i}\left(\sqrt{a^2 - x_{i-1}^2} - \sqrt{a^2 - x_i^2}\right) - \right.$$

$$\left.\frac{x_iS_{i-1} - x_{i-1}S_i}{x_{i-1} - x_i}\left(\sin^{-1}\frac{x_i}{a} - \sin^{-1}\frac{x_{i-1}}{a}\right)\right\} + $$

$$\sum_{i=1}^{n}\left\{\frac{S_{mRi-1} - S_{mRi}}{x_{i-1} - x_i}\left(\sqrt{a^2 - x_{i-1}^2} - \sqrt{a^2 - x_i^2}\right) - \right.$$

$$\left.\frac{x_iS_{mRi-1} - x_{i-1}S_{mRi}}{x_{i-1} - x_i}\left(\sin^{-1}\frac{x_i}{a} - \sin^{-1}\frac{x_{i-1}}{a}\right)\right\} = \frac{\pi\lambda\sigma_{CY}}{4a} \quad (3)$$

The tip position a of the tensile plastic zone is calculated by the equation (3). The tip position $\omega^+$ of the tensile plastic zone in this cycle becomes a.

Therefore, crack opening displacement $V(x_j)$ at $x_j$ is represented as follows.

[Equation 5]

$$V(x_j) = P\sum_{i=1}^{n}\int_{x_{i-1}}^{x_i}\left\{\frac{S_i - S_{i-1}}{x_i - x_{i-1}}x - \frac{x_{i-1}S_i - x_iS_{i-1}}{x_i - x_{i-1}}\right\}F(x_j, x, a)dx + \quad (4)$$
$$\sum_{i=1}^{n}\int_{x_{i-1}}^{x_i}\left\{\frac{S_{mRi} - S_{mRi-1}}{x_i - x_{i-1}}x - \frac{x_{i-1}S_{mRi} - x_iS_{mRi-1}}{x_i - x_{i-1}}\right\}F(x_j, x, a)dx -$$
$$\lambda\sigma_{CY}\int_0^a F(x_j, x, a)dx$$

wherein,

[Equation 6]

$$F(x_j, x, a)dx = \begin{cases} \frac{8}{\pi E'}\tanh^{-1}\sqrt{\frac{a^2 - x^2}{a^2 - x_j^2}} & (x_j < x) \\ \frac{8}{\pi E'}\coth^{-1}\sqrt{\frac{a^2 - x^2}{a^2 - x_j^2}} & (x < x_j) \end{cases} \quad (5)$$

Wherein, $$E' = \begin{cases} E \\ E/(1 - v^2) \end{cases}$$

E: plane stress condition
$E/(1-v^2)$: plane strain condition
E: Young's modulus, v: Poisson ratio From the (factitious) crack opening displacement $V(x_j)$ obtained from the equations (4) and (5) (a rod with this length is disposed in the position $x_j$ of this crack and elastic stress with tensile yield is applied on both ends of the rod, so that the length of the rod released from the elastic stress becomes the inherent displacement), the inherent displacement $L(x_j)$ at the maximum load is represented as follows.

[Equation 7]

$$L(x_i) = \frac{V(x_i)}{\left(1 + \frac{\lambda\sigma_{CY}}{E'}\right)} \quad (6)$$

The second operation means 12 calculates the inherent displacement, the tip position of the compressive plastic zone, and t inherent displacement at the minimum load (step S102).

The crack opening displacement in an unloading process is represented as follows.

[Equation 8]

$$V(x_j) = P\sum_{i=1}^{n}\int_{x_{i-1}}^{x_i}\left\{\frac{S_i - S_{i-1}}{x_i - x_{i-1}}x - \frac{x_{i-1}S_i - x_iS_{i-1}}{x_i - x_{i-1}}\right\}F(x_j, x, a)dx + \quad (7)$$
$$\sum_{i=1}^{n}\int_{x_{i-1}}^{x_i}\left\{\frac{S_{mRi} - S_{mRi-1}}{x_i - x_{i-1}}x - \frac{x_{i-1}S_{mRi} - x_iS_{mRi-1}}{x_i - x_{i-1}}\right\}F(x_j, x, a)dx +$$
$$\sum_{i=1}^{n}\int_{x_{i-1}}^{x_i}\left\{\frac{\sigma_i - \sigma_{i-1}}{x_i - x_{i-1}}x - \frac{x_{i-1}\sigma_i - x_i\sigma_{i-1}}{x_i - x_{i-1}}\right\}F(x_j, x, a)dx$$

The crack opening displacement in a case where elastic stress $\sigma_j$ is applied on the segment of which thickness is equal to the inherent displacement is expressed as follows.

[Equation 9]

$$V(x_j) = L(x_j)\left(1 + \frac{\sigma_j}{E'}\right) \quad (8)$$

The equations (7) and (8) are equal in the position of an elastic state at the minimum load. P in the equation (7) is a value of the minimum load, and $L(x_j)$ in the equation (8) is the inherent displacement at the effective maximum load immediately before. Thus, equalizing the equations (7) and (8) to set up an equation of $\sigma_j$ and calculating the equation with convergence using a Gauss-Seidel method make it possible to obtain operating stress distribution at the minimum load. During this convergence process, the following substitutions may be made.

[Equation 10]

If $\zeta_{+1}\sigma_j < -\lambda\sigma_Y$, $\zeta_{+1}\sigma_j = -\lambda\sigma_Y$ If $\zeta_{+1}\sigma_j > -\lambda\sigma_Y$, $\zeta_{+1}\sigma_j = \lambda\sigma_Y$ (9)

Substituting obtained stress into the equation (7) makes it possible to obtain the crack opening displacement at the minimum load.

Figure 5:
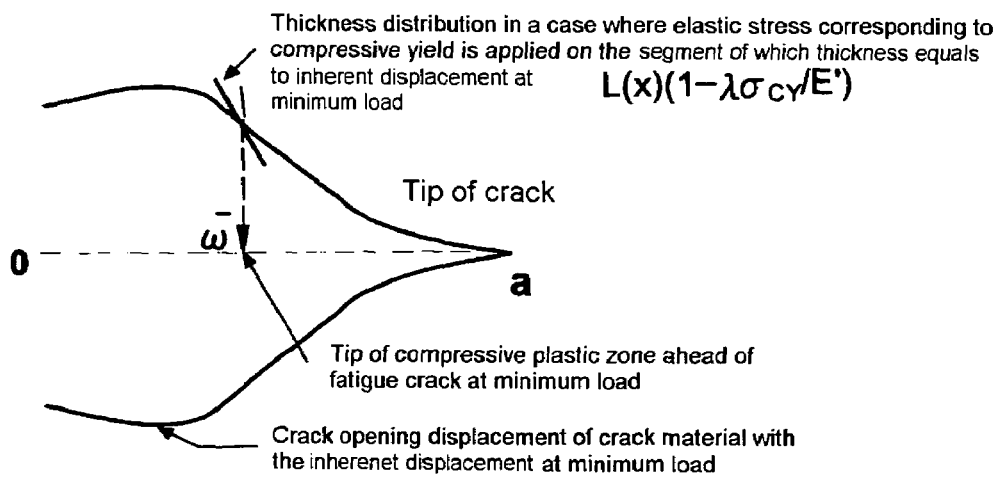
FIG. 5 is a drawing showing a method for determining the tip position of a compressive plastic zone.

FIG. 5 shows a method for determining the tip position of the compressive plastic zone. As shown in FIG. 5, the position of an intersection point of a curve in a case where the inherent displacement L(x) at the maximum load is elastically shrunk in accordance with a compressive yield and the crack opening displacement V(x) at the minimum load becomes the tip position $\omega^-$ of the compressive plastic zone at the minimum load.

In the compressive yield zone, the inherent displacement L(x) is replaced as follows.

[Equation 11]

$$L(x_i) = \frac{V(x_i)}{\left(1 - \frac{\lambda\sigma_{CY}}{E'}\right)} \quad (10)$$

The third operation means 13 calculates the fatigue damage accumulated region formed ahead of the crack, and calculates the increment of the crack from the size of the fatigue damage accumulated region to add the increment to the crack length (step S103).

Comparing the tip position $\omega^+$ of the tensile plastic zone and the tip position $\omega^-$ of the compressive plastic zone, the smaller one is set as $\omega'$. Using the following equation 12,

[Equation 12]

$$\omega = \omega' - c$$

the fatigue damage accumulated region $$\omega$$

is obtained.

When the load amplitude varies every cycle, the increment $\Delta c$ of the crack is represented by the following equation 14 by using equation 13.

[Equation 13]

$$dc/dN = C(\omega)^m$$

[Equation 14]

$$\Delta c = C(\omega' - c_b)^m \qquad (11)$$

Wherein, $\Delta N=1$. $c_b$ represents the previous crack length and $c_c$ represents a new crack length. The new crack length $c_c = c_b + \Delta c$.

When the constant load amplitude continues for a while, the number of cycles is obtained by the following equation (12) with considering that an upper limit for the increment of the crack which can advance at a time by calculation is 5% of the fatigue damage accumulated region $\omega$.

[Equation 15]

$$\Delta N = \frac{1}{C} \int_{c_b}^{c_c} \frac{dx}{(\omega' - x)^m} \qquad (12)$$

Then the increment of the crack is obtained from the equation (11). Wherein,

[Equation 16]

If $0.05\omega' - 0.95 c_b < 0.5d$, $c_c = 0.05\omega' - 0.95 c_b$

If $0.05\omega' - 0.95 c_b \geq 0.5d$, $c_c = 0.5d$ (13)

holds.

The fourth operation means 14 judges whether or not the crack length obtained in the step S103 reaches a half of the diameter of the first grain (step S104).

How to obtain the increment of plastic strain and the cumulative plastic strain will be described.

Figure 6A:
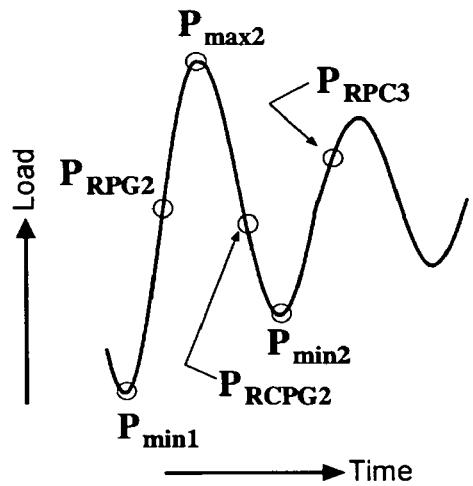
FIG. 6A is a drawing showing part of a load cycle.
Figure 6B:
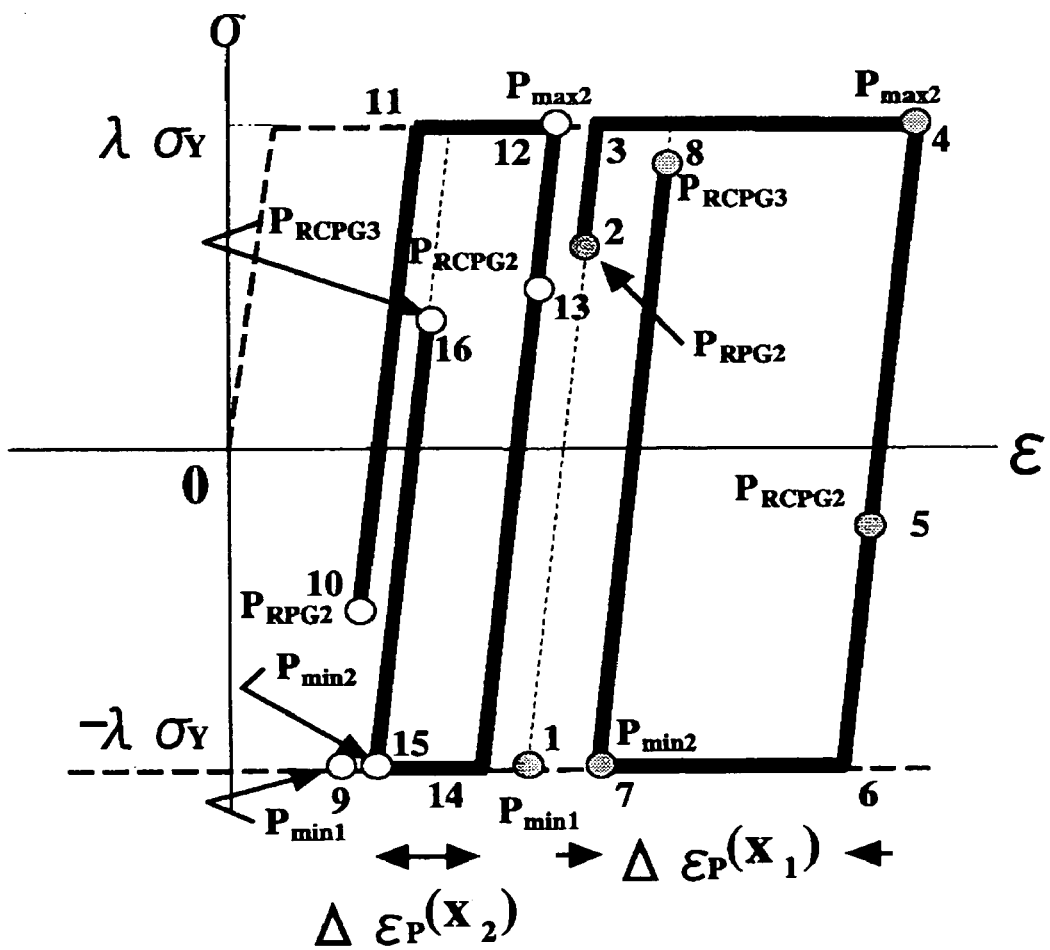
FIG. 6B is a drawing showing the history of stress and strain in a cyclic plastic zone in a load cycle in which a tensile plastic zone at a maximum load is larger than a compressive plastic zone at a minimum load.
Figure 6C:
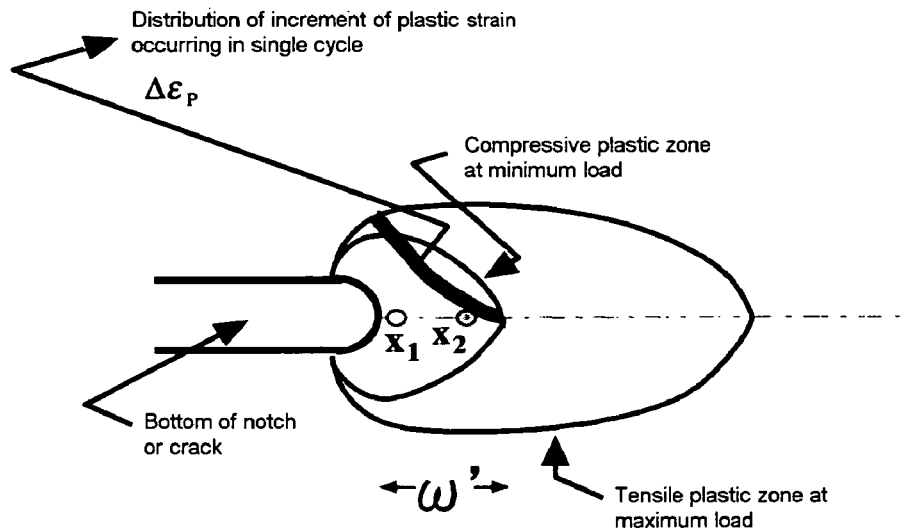
FIG. 6C is a drawing for explaining an increment of plastic strain occurring in the notch or the tip position of the crack.
Figure 7:
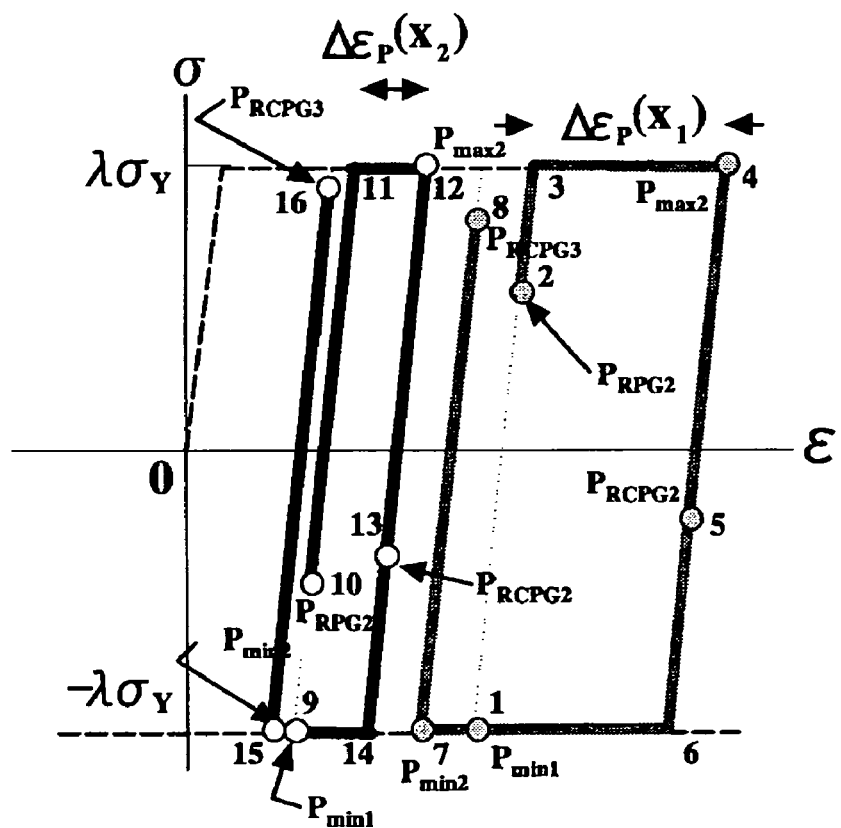
FIG. 7 is a drawing showing the history of stress and strain in a cyclic plastic zone in a load cycle in which the tensile plastic zone at the maximum load is smaller than the compressive plastic zone at the minimum load.

FIG. 6A shows part of a load cycle. FIG. 6B shows the history of stress and strain in a cyclic plastic zone in a load cycle in which the tensile plastic zone at the maximum load is larger than the compressive plastic zone at the minimum load. FIG. 6C is a drawing for explaining the increment of plastic strain occurring in the notch or the tip position of the crack. FIG. 7 shows the history of stress and strain in the cyclic plastic zone in a load cycle in which the tensile plastic zone at a load is smaller than the compressive plastic zone at the minimum load.

Considering the increment of plastic strain in the positions $x_1$ and $x_2$ ($x_1$ is nearer to the tip of a crack or the bottom of a notch: refer to FIG. 6C) ahead of a crack (or the bottom of a notch) formed in a cycle from a minimum load $P_{min1}$ to immediately after the next minimum load $P_{min2}$ when a fluctuating load as shown in FIG. 6A is applied. If the compressive plastic zone is formed at the time of $P_{min1}$ and both of $x_1$ and $x_2$ are positioned in the plastic zone, the positions $x_1$ and $x_2$ correspond to positions indicated with 1 and 9 in a graph of stress and strain of FIG. 6B.

Operation enters a loading process from this time on. The whole comes into an elastic state (including unloading elasticity) even if a crack closing zone is not formed at $P_{min1}$, so that the relation between stress and strain linearly moves from "1" to "2" and "9" to "10" as shown in FIG. 6B in the graph of stress and strain. Thus, the tensile plastic zone is formed from the tip of the crack (the bottom of the notch at first), and the tensile plastic zone is increased with increase in a load from a load at which the plastic zone starts growing, that is, a re-tensile plastic zone's generated load $P_{RPG}$. Therefore, the relation between stress and strain gets near to "3" or "11" being plastic positions in the graph of stress and strain at the re-tensile plastic zone's generated load with getting near to the tip of the crack. Then, a distance from yield to a maximum load $P_{max2}$ in the graph of stress and strain becomes long with getting near to the tip of the crack, and hence the relations between stress and strain come to "4" and "12" at the maximum load $P_{max2}$ in the positions $x_1$ and $x_2$, respectively.

Operation enters an unloading process from this time on. Since every part becomes the (unloaded) elastic state, stress and strain are linearly reduced. The compressive plastic zone starts growing from the tip of the crack (the bottom of the notch at first) at a re-compressive plastic zone's generated load $P_{RCPG}$. Further unloading, the compressive plastic zone grows, and the relation between stress and strain follows a trail of "5", "6", and "7" in the position of $x_1$ and a trail of "13", "14", and "15" in the position of $x_2$ and then reaches a minimum load $P_{min2}$. Upon entering a loading process again, the relation between stress and strain follows trails of "7" to "8" and "15" to "16" and shown in FIG. 6B.

By the way, the cyclic plastic energy applied in one cycle is represented by the product of the increment of plastic strain and elastic stress amplitude in perfect elastic plastic bodies. FIG. 6B shows the history of stress and strain in the cyclic plastic zone in the load cycle in which the tensile plastic zone at the maximum load is larger than the compressive plastic zone at the minimum load. In this case, as shown in FIG. 6B, the increment of strain from a compressive yield to the minimum load corresponds to the increment of plastic strain. In a load cycle in which the tensile plastic zone at the maximum load is smaller than the compressive plastic zone at the minimum load, on the other hand, as shown in FIG. 7, the increment of strain from a tensile yield to the maximum load corresponds to the increment of plastic strain.

In other words, in the load cycle in which the tensile plastic zone at the maximum load is larger than the compressive plastic zone at the minimum load, the difference of strain between "6" and "7" of FIG. 6B may be defined in the position of $x_1$ and the difference of strain between "14" and "15" may be defined in the position of $x_2$ as the increment of plastic strain in one cycle. As shown in FIG. 6C, the distribution of the increment of plastic strain formed only in the compressive plastic zone at the minimum load becomes "0" at the end of the compressive plastic zone and becomes larger with reaching the tip of the crack. The distribution of the increment of plastic strain is represented as follows on the basis of a crack opening displacement $V(x)_{Pmin}$ at the minimum load.

[Equation 17]

$$\Delta\varepsilon_p(x) = \frac{L(x) - V_{p\min}(x)/(1 - \lambda\sigma_Y/E)}{L(x)} \quad (14)$$

wherein, L(x) represents the inherent displacement at the maximum load $P_{min2}$.

In the load cycle in which the tensile plastic zone at the maximum load is smaller than the compressive plastic zone at the minimum load, on the other hand, the difference of strain between "3" and "4", of FIG. 7 may be defined in the position of $x_1$ and the difference of strain between "11" and "12" may be defined in the position of $x_2$ as the increment of plastic strain in one cycle. The distribution of the increment of plastic strain formed only in the tensile compressive plastic zone at the maximum load becomes "0" at the end of the zone and becomes larger with reaching the tip of the crack. The distribution of the increment of plastic strain is represented as follows on the basis of a crack opening displacement $V(x)_{Pmax}$ at the maximum load.

[Equation 18]

$$\Delta\varepsilon_p(x) = \frac{V(x)_{p\max}/(1 - \lambda\sigma_Y/E) - L(x)}{L(x)} \quad (15)$$

wherein, L(x) represents the inherent displacement at the maximum load $P_{min1}$.

Accordingly, the cumulative plastic strain $[\Sigma\Delta\varepsilon_p(x)]_c$ accumulated at the time when the crack length comes to $C_c$ is represented as follows.

[Equation 19]

$$\left[\sum \Delta\varepsilon_p(x)\right]_c = \left[\sum \Delta\varepsilon_p(x)\right]_b + N\Delta\varepsilon_p(x) \quad (16)$$

wherein, $[\Sigma\Delta\epsilon_p(x)]_b$ is the cumulative plastic strain after the previous calculation cycle and N is the number of cycles ("1" under the fluctuating load).

In the first grain, if a constant amplitude load is continued for a while, the cumulative plastic strain is calculated by the following method. Considering that an upper limit for the increment of the crack which can advance at a time by calculation is 5% of the fatigue damage accumulated region $\omega$, the number of cycles is obtained by the following equation (17) based on

[Equation 20]

$$dc/dN = C(\tilde{\omega})^m$$

[Equation 21]

$$N = \frac{1}{C}\int_{c_b}^{c_c} \frac{dx}{(\omega' - x)^m} \quad (17)$$

and then the cumulative plastic strain may be obtained from equation (16).

Figure 8:
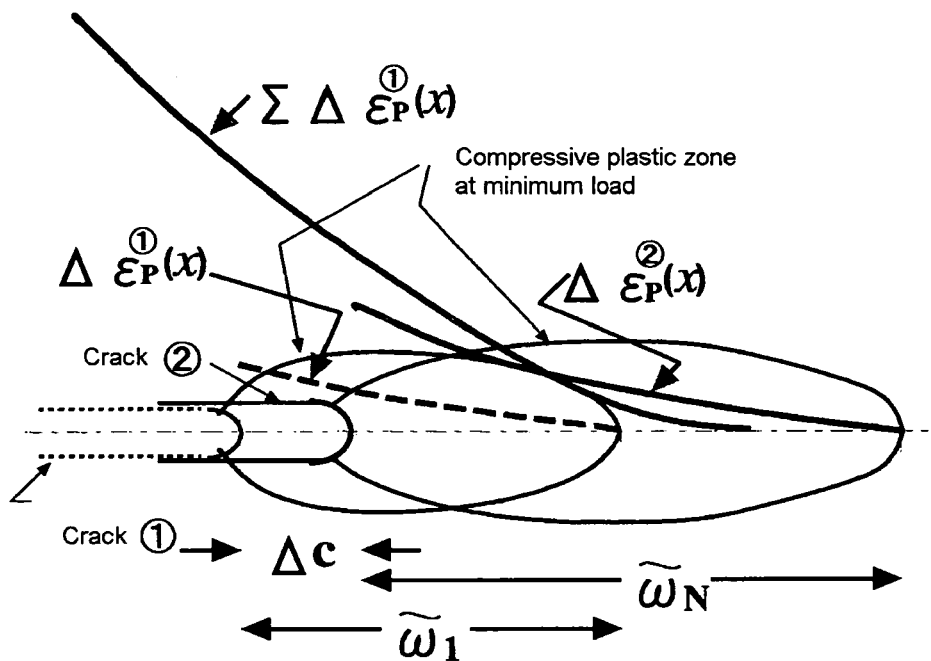
FIG. 8 is a drawing for explaining how to deal with cumulative plastic strain in the case of propagating the crack at a time under a certain load amplitude.
Figure 9A:
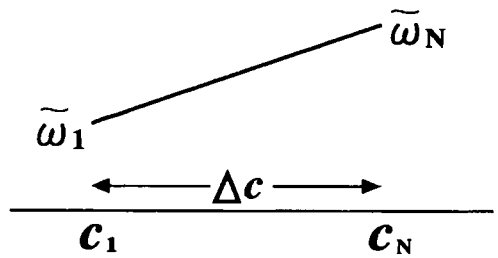
FIG. 9A is a drawing showing the linear assumption of a change in the size of the compressive plastic zone in $\Delta c$.
Figure 9B:
FIG. 9B is a drawing showing the linear assumption of a change in compressive plastic strain in $\Delta c$.
Figure 9B:
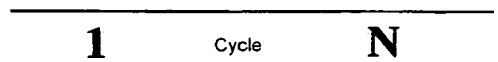

Operation in a case where the constant amplitude load continues for a while outside of the first grain will be described with reference to FIGS. 8 and 9. FIG. 8 is a drawing for explaining how to deal with the cumulative plastic strain in the case of propagating the crack at a time under the certain amplitude load. FIG. 9A shows the linear assumption of a change in the size of the fatigue damage accumulated region in $\Delta c$, and FIG. 9B shows the linear assumption of a change in the plastic strain in $\Delta c$.

Also at the outside of the first grain, as with calculation in the inside of the grain, it is considered that an upper limit for the increment of the crack which can advance at a time by calculation is 5% of the fatigue damage accumulated region $\omega$.

In this case, $\omega$ at this point in time is set at $\omega_1$.

Then, $\omega$ after propagation is obtained as shown in FIG. 8 and this is set to $\omega_N$.

It is idealized that $\omega$ linearly varies in $\Delta c$ as shown in FIG. 9A. In other words, the following equation (18) holds.

[Equation 22]

$$\frac{dc}{dN} = C\tilde{\omega} = C(a_1 c + a_2)^m \quad (18)$$

wherein, the following equation (20) holds based on equation (19)

[Equation 23]

$$a_1 = \frac{\tilde{\omega}_N - \tilde{\omega}_1}{c_N - c_1},$$

$$a_2 = \frac{c_N \tilde{\omega}_1 - c_1 \tilde{\omega}_N}{c_N - c_1} \quad (19)$$

[Equation 24]

$$N = \frac{1}{C}\int_{c_1}^{c_N}(a_1 c + a_2)^m dc = \frac{(\tilde{\omega}_N - \tilde{\omega}_1)(\tilde{\omega}_N^{1-m} - \tilde{\omega}_1^{1-m})}{C(1-m)\Delta c} \quad (20)$$

Accordingly, N cycles are needed to propagate a distance of $\Delta c$.

Wherein, $\Delta\epsilon_{P1}(x)$ represents the increment of plastic strain in one cycle in the previous fatigue damage accumulated region, and $\Delta\epsilon_{P2}(x)$ represents the increment of plastic strain in one cycle after being propagated $\Delta c$. By first-order approximation in which plastic strain linearly varies from $\Delta\epsilon_{P1}(x)$ to $\Delta\epsilon_{P2}(x)$ with respect to the number of cycles, as shown in FIG. 9B, the cumulative plastic strain $\Delta\epsilon_{P2}(x)$ applied in a position of x until the time comes when the crack becomes "crack 2" of FIG. 8 is represented by the following equation.

[Equation 25]

$$\sum \Delta\varepsilon_{p2}(x) = \sum \Delta\varepsilon_{p1}(x) + \sum_{i=0}^{N-1}\left(\sum \Delta\varepsilon_{p1}(x) + i\frac{\sum \Delta\varepsilon_{p2}(x) - \sum \Delta\varepsilon_{p1}(x)}{N-1}\right) = \sum \Delta\varepsilon_{p1}(x) + 0.5N\left(\sum \Delta\varepsilon_{p1}(x) + \sum \Delta\varepsilon_{p2}(x)\right) \quad (21)$$

When the crack length is judged to be smaller than half of the diameter of the first grain in the step S104, the fourth operation means 14 sets the increment of plastic strain to "0" (step S105). The fourth operation means 14 also calculates the cumulative plastic strain from the increment of plastic strain at the outside of the first grain by a method described above (step S106).

When it is judged that the crack length becomes half of the diameter of the first grain or more in the step S104, the fourth operation means 14 calculates the cumulative plastic strain from the increment of plastic strain by the method described above (step S107).

Next, in the inside of the first grain, whether or not the cumulative plastic strain calculated in the step S107 reaches the ductility limit specific to the material is judged (step S108). If the cumulative plastic strain reaches the ductility limit specific to the material, it is judged that that position has been changed into the opening mode crack. Thus, in each position inside the first grain, the crack mode index $\delta(x_i)=0$ (step S109).

At the outside of the first grain, the inherent displacement taken in a crack incremental region is calculated from the cumulative plastic strain (step S110).

Figure 10:
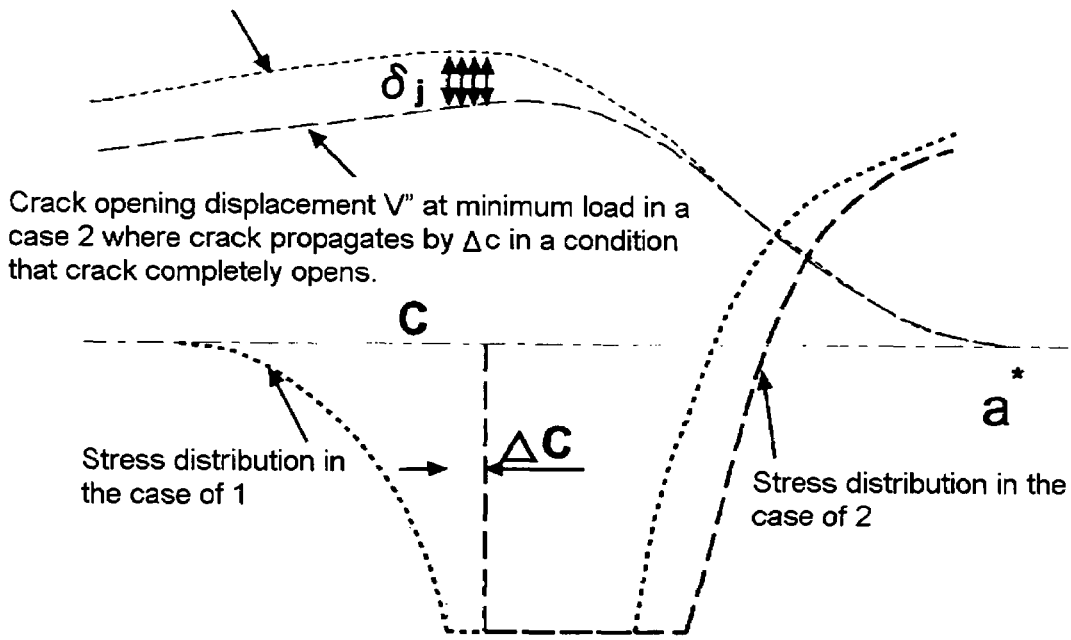
FIG. 10 is a drawing showing plastic compression released when a crack propagates.

A load level at which the crack closes depends on whether the moment at which the crack propagates into the cyclic plastic zone is in the vicinity of the minimum load or in the vicinity of the maximum load. FIG. 10 schematically shows crack opening displacement V' in a case where a load has reached its minimum without propagating the crack, and crack opening displacement V" at the minimum load in a case where the crack propagates by $\Delta c$ without forming a clack closing zone. To obtain V', the following equation (22) is equalized with the following equation (23).

[Equation 26]

$$V(\overline{x}_j) = P\sum_{i=1}^{n}\int_{x_{i-1}}^{x_i}\left\{\frac{S_i - S_{i-1}}{x_i - x_{i-1}}x - \frac{x_{i-1}S_i - x_iS_{i-1}}{x_i - x_{i-1}}\right\}F(\overline{x}_j, x, a)dx +$$

$$\sum_{i=1}^{n}\int_{x_{i-1}}^{x_i}\left\{\frac{S_{mRi} - S_{mRi-1}}{x_i - x_{i-1}}x - \frac{x_{i-1}S_{mRi} - x_iS_{mRi-1}}{x_i - x_{i-1}}\right\}F(\overline{x}_j, x, a)dx +$$

$$\sum_{i=0}^{k}\delta(i)\sigma_i\left\{\zeta(i)\int_{x_{i-1}}^{x_i}\frac{x - x_{i-1}}{x_i - x_{i-1}}F(\overline{x}_j, x, a)dx - \xi(i)\int_{x_i}^{x_{i+1}}\frac{x - x_{i+1}}{x_{i+1} - x_i}F(\overline{x}_j, x, a)dx\right\} +$$

-continued $$\sum_{i=k+1}^{l+1}\sigma_i\left\{\zeta(i)\int_{x_{i-1}}^{x_i}\frac{x - x_{i-1}}{x_i - x_{i-1}}F(\overline{x}_j, x, a)dx - \xi(i)\int_{x_i}^{x_{i+1}}\frac{x - x_{i+1}}{x_{i+1} - x_i}F(\overline{x}_j, x, a)dx\right\} +$$

$$\sum_{i=l+1}^{n}\sigma_{i+1}\left\{\zeta(i)\int_{x_{i-1}}^{x_i}\frac{x - x_{i-1}}{x_i - x_{i-1}}F(\overline{x}_j, x, a)dx - \xi(i)\int_{x_i}^{x_{i+1}}\frac{x - x_{i+1}}{x_{i+1} - x_i}F(\overline{x}_j, x, a)dx\right\}$$

(22)

wherein, $\zeta(0)=0$, $\xi(k+1)=0$, $\zeta(l+1)=0$, $\xi(n+1)=0$, and $\zeta(i)=\xi(i)=1$ as for the others.

[Equation 27]

$$V(\overline{x}_j) = L(\overline{x}_j)\left(1 + \frac{kk(j)\sigma_{j-1} + \sigma_j}{jk(j)E'}\right).$$

$$kk(j) = \begin{cases} 0 & (j \neq n+1) \\ 1 & (j = n+1) \end{cases}$$

$$jk(j) = \begin{cases} 1 & (j \neq n+1) \\ 2 & (j = n+1) \end{cases}$$

wherein, $L(\overline{x}_j)$ is the inherent displacement formed at the maximum load immediately before . . . . (23)

Then, the equality equation is changed into the shape of $\sigma_j=$, and is solved on the condition of the equation (9) by using the Gauss-Seidel method. Then, substituting obtained $\sigma_j$ into the equation (22) can get V'.

To obtain V", on the other hand, the following equation (24) is equalized with the following equation (23) with considering that a double point is disposed at i=l+1 in $\sigma_i$.

[Equation 28]

$$V(\overline{x}_j) = P_{max}\sum_{i=1}^{n}\int_{x_{i-1}}^{x_i}\left\{\frac{S_i - S_{i-1}}{x_i - x_{i-1}}x - \frac{x_{i-1}S_i - x_iS_{i-1}}{x_i - x_{i-1}}\right\}F(\overline{x}_j, x, a)dx +$$

$$\sum_{i=1}^{n}\int_{x_{i-1}}^{x_i}\left\{\frac{S_{mRi} - S_{mRi-1}}{x_i - x_{i-1}}x - \frac{x_{i-1}S_{mRi} - x_iS_{mRi-1}}{x_i - x_{i-1}}\right\}F(\overline{x}_j, x, a) +$$

$$\sum_{i=0}^{k}\delta(i)\sigma_i\left\{\zeta(i)\int_{x_{i-1}}^{x_i}\frac{x - x_{i-1}}{x_i - x_{i-1}}F(\overline{x}_j, x, a)dx - \xi(i)\int_{x_i}^{x_{i+1}}\frac{x - x_{i+1}}{x_{i+1} - x_i}F(\overline{x}_j, x, a)dx\right\} +$$

$$\sum_{i=l+1}^{n}\sigma_{i+1}\left\{\zeta(i)\int_{x_{i-1}}^{x_i}\frac{x - x_{i-1}}{x_i - x_{i-1}}F(\overline{x}_j, x, a)dx - \xi(i)\int_{x_i}^{x_{i+1}}\frac{x - x_{i+1}}{x_{i+1} - x_i}F(\overline{x}_j, x, a)dx\right\}$$

(24)

wherein, $x_{l+1}=c+\Delta c$, $\zeta(0)=0$, $\xi(k)=0$, $\zeta(l+1)=0$, $\xi(n+1)=0$, and $\zeta(i)=\xi(i)=1$ as for the others.

Then, the equality equation is changed into the shape of $\sigma_j=$, and is solved on the condition of the equation (9) by using the Gauss-Seidel method. Then, substituting obtained $\sigma_j$ into the equation (24) can get V".

Thus, $\delta j = V' - V''$ holds from FIG. 10. It is conceivable that the inherent displacement practically taken in the actual crack is between $V'+\delta_j$ and $V'-\delta_j$, and its ratio is proportional to the $\Sigma$ cumulative plastic strain $\Delta\epsilon_{p2}(x)$ accumulated until the crack occurs.

Accordingly, the inherent displacement in the point of producing a new fracture is obtained from the following equation (25).

[Equation 29]

$$L(\bar{x}_j) = \frac{1}{1 - \lambda\sigma_Y/E'}(V'_j - k\sigma_j) \quad (25)$$

Wherein, k is as follows.

[Equation 30]

$$k = \begin{cases} \alpha\sum \Delta\varepsilon_{p2}(x) & \left(\text{in the case of } \left|\alpha\sum \Delta\varepsilon_{p2}(x)\right| \leq 1\right) \\ 1 & \left(\text{in the case of } \left|\alpha\sum \Delta\varepsilon_{p2}(x)\right| \geq 1\right) \\ -1 & \left(\text{in the case of } \left|\alpha\sum \Delta\varepsilon_{p2}(x)\right| < -1\right) \end{cases} \quad (26)$$

wherein, $\alpha$ is a plastic contraction coefficient and a material constant.

The fifth operation means 15 calculates the yield stress under the cyclic load at the next maximum load (step S111).

The crack inside the first grain changed from a mixed mode type in which the shear mode crack and the opening mode crack are mixed to an opening type does not have charge of the tensile stress. When the tip position a of the tensile plastic zone grows over a past tip position a' of the tensile plastic zone at the maximum load, the following equation (27) holds.

[Equation 31]

$$\int_0^a \{P_{max}S(x) + s_{mR}(x)\}g(x, a)dx - \lambda\sigma_Y \sum_{i=1}^k \delta(i)\int_{x_i}^{x_{i+1}} g(x, a)dx - \lambda\sigma_Y \int_c^a g(x, a)dx = 0 \quad (27)$$

wherein, $\sigma_Y$ is a yield stress at the previous minimum load. In this case, the yield stress is increased from a proportional limit by work hardening and the tip position a of the tensile plastic zone is held in the past tip position a' of the tensile plastic zone as long as the yield stress $\sigma_Y$ does not exceed a static yield stress $\sigma_{YS}$, so that the following equation (28) holds.

[Equation 32]

$$\sigma_Y = \frac{\int_0^{a'}\{P_{max}S(x) + s_{mR}(x)\}g(x, a')dx}{\lambda\left[\int_c^{a'} g(x, a')dx - \sum_{i=1}^k \delta(i)\int_{x_i}^{x_{i+1}} g(x, a')dx\right]} \quad (28)$$

wherein, if the yield stress $\sigma_Y$ exceeds the static yield stress $\sigma_{YS}$, the yield stresses after that become $\sigma_{YS}$.

If the yield stress $\sigma_Y$ is smaller than the previous yield stress, the work hardening does not progress and the yield stress $\sigma_Y$ stays on the previous yield stress.

After the yield stress under the next cyclic load is obtained in the step S111, the processing returns to the step S101. At this time, when the yield stress $\sigma_Y$ obtained from the equation (28) is larger than the static yield stress $\sigma_{YS}$, it is necessary to re-obtain the tip position a of the tensile plastic zone by the equation (27) by substituting the static yield stress $\sigma_{YS}$ for the yield stress $\sigma_Y$ of the equation (27)

When the tip position a of the tensile plastic zone is away from and beyond the past tip position a' of the tensile plastic zone, the crack opening displacement V is obtained as follows.

[Equation 33]

$$V(\bar{x}_j) = P\sum_{i=1}^n \int_{x_{i-1}}^{x_i} \left\{\frac{S_i - S_{i-1}}{x_i - x_{i-1}}x - \frac{x_{i-1}S_i - x_i S_{i-1}}{x_i - x_{i-1}}\right\}F(\bar{x}_j, x, a)dx + \sum_{i=1}^n \int_{x_{i-1}}^{x_i} \left\{\frac{s_{mRi} - s_{mRi-1}}{x_i - x_{i-1}}x - \frac{x_{i-1}s_{mRi} - x_i s_{mRi-1}}{x_i - x_{i-1}}\right\}F(\bar{x}_j, x, a)dx - \lambda\sigma_Y \sum_{i=1}^k \int_{x_{i-1}}^{x_i}(\delta(i) - \delta(i-1))F(x_j, x, a)dx - \lambda\sigma_Y \int_c^a F(\bar{x}_j, x, a)dx \quad (29)$$

The crack opening displacement V is obtained from an equation (29).

Thus, the inherent displacement from c to a ahead of the crack and in a position of $\delta(i)=1$ are obtained by the following equation (30).

[Equation 34]

$$L(\bar{x}_j) = V(\bar{x}_j)\bigg/\left(1 + \frac{\lambda\sigma_Y}{E'}\right) \quad (30)$$

The inherent displacement in the other points are kept at the previous ones. The tip position $\omega^+$ of the tensile plastic zone becomes a.

When the yield stress $\sigma_y$ obtained from the equation (28) is smaller than the previous yield stress, the tip position a of the tensile plastic zone is positioned inside of the past tip position a' of the tensile plastic zone. Also in this case, it is necessary to obtain operating stress distribution at the maximum load by using the equation (22) and the crack opening displacement in returning to the step S101.

When the tip position a of the tensile plastic zone is positioned inside of the tip position a' of the tensile plastic zone, the equations (22) and (23) are equalized. The equality equation is changed into the shape of $\sigma_j=$, and the following substitutions are made in the process of convergence by using the Gauss-Seidel method.

[Equation 35]

in the case of $x_i \leq d$ and $\delta(i)=1$, or $c \leq x_i \leq a$, $$\text{if }_{\zeta+1}\sigma_j < -\lambda\sigma_Y, _{\zeta+1}\sigma_j = -\lambda\sigma_Y \quad (31)$$

$$\text{if }_{\zeta+1}\sigma_j > \sigma_Y, _{\zeta+1}\sigma_j = \lambda\sigma_Y$$

[Equation 36]

in the case of $x_i \leq d$ and $\delta(i)=0$, or $c_0 \leq x_i \leq a$, $$\text{if }_{\zeta+1}\pi_j < -\lambda\sigma_Y, _{\zeta+1}\sigma_j = -\lambda\sigma_Y \quad (32)$$

$$\text{if }_{\zeta+1}\sigma_j > 0_Y, _{\zeta+1}\sigma_j = 0$$

Converged $\sigma_j$ is the operating stress distribution at the maximum load. Substituting this into the equation (22) makes it possible to obtain the crack opening displacement V at the maximum load.

Figure 11:
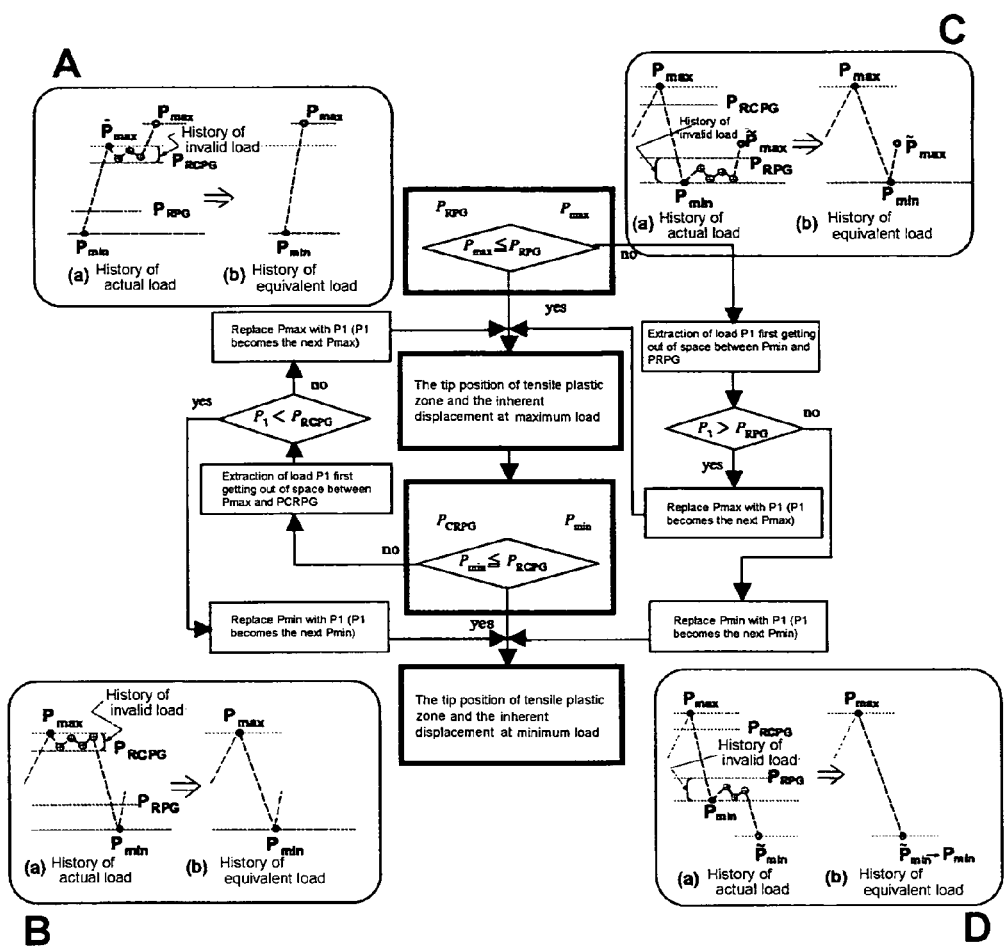
FIG. 11 is a drawing showing the system of extracting only a load pair contributing to crack growth.

Next, in the method of estimating the fatigue crack growth curve according to the present invention, the system of extracting only a load pair contributing to the growth of the crack will be described on the basis of FIG. 11. FIG. 11 is a drawing showing the system of extracting only the load pair contributing to the growth of the crack.

First, after ending the step S101, the re-compressive plastic zone's generated load $P_{RCPG}$ is obtained in a step S201.

When the tip position of the crack is inside the first grain, the re-compressive plastic zone's generated load $P_{RCPG}$ is obtained by the following method.

The crack opening displacement at the re-compressive plastic zone's generated load is represented by the equation (22). Using the inherent displacement at the previous minimum load, the equation (23) holds in an elastic zone. The equations (22) and (23) are equalized, and an equation in the shape of $\sigma_j=(j=k+1, n)$ and an equation in the shape of $P=(j=k)$ are made. Then, $\sigma_j=-\lambda\sigma_{CY}$ holds with respect to the crack tip position $j=k+1$. Then, solving the equation by using the Gauss-Seidel method to obtain the following equation (33),

[Equation 37]

$$V(c_c) = \left(1 + \frac{\lambda\sigma_Y}{E}\right)L(c_c) \quad (33)$$

obtained P becomes the re-compressive plastic zone's generated load $P_{RCPG}$.

When the following load pair ($P_{min}$, $P_{max}$) is positioned between $P_{max}$ and $P_{RCPG}$ (A in FIG. 11), the load pair does not cause the initiation and growth of the crack. This load pair is called an invalid load pair, and the other load pair is called a valid load pair. In a case where a maximum load first gets out of this load space, if the maximum load is larger than a past maximum load $P_{bmax}$, the processing returns to the step S101 to calculate the tip position a of a factitious crack and a tensile plastic zone tip $\omega^+$. If the maximum load is smaller than the past maximum load, the equations (22) and (23) are formulated by the Gauss-Seidel method and the operating stress distribution is obtained within the confines of the equations (31) and (32). Then, substituting it into the equation (22) can obtain the crack opening displacement. In a case where a minimum load first gets out of the space between $P_{max}$ and $P_{RCPG}$ (B in FIG. 11), the processing goes ahead.

When the following load pair ($P_{min}$, $P_{max}$) is positioned between $P_{max}$ and $P_{RCPG}$, the load pair does not cause the initiation and growth of the crack. This load pair becomes the invalid load pair. In a case where the maximum load first gets out of this load space, if the maximum load is larger than the past maximum load $P_{bmax}$ (A in FIG. 11), the processing returns to the step S101 to re-calculate the tip position a of the factitious crack and the tensile plastic zone tip $\omega^+$. When the minimum load first gets out of the space between $P_{max}$ and $P_{RCPG}$ (B in FIG. 11), the processing goes ahead.

Furthermore, after ending the step S102, the re-compressive plastic zone's generated load $P_{RPG}$ is calculated in a step S202.

When the tip position of the crack is inside the first grain, the re-compressive plastic zone's generated load $P_{RPG}$ is obtained by the following method.

The crack opening displacement at the re-compressive plastic zone's generated load is represented by the equation (22). Using the inherent displacement obtained at the previous minimum load, the equation (23) holds in the elastic zone. The bottom of the notch in the grain becomes a tensile plastic zone and the first grain boundary becomes a tensile elastic plastic boundary at the re-tensile plastic zone's generated load, so that $\sigma_j=\lambda\sigma_{CY}$ holds with respect to the crack tip position $j=k+1$. Then, solving the equation by using the Gauss-Seidel method to obtain the following equation (34),

[Equation 38]

$$V(c_c) = \left(1 - \frac{\lambda\sigma_Y}{E}\right)L(c_c) \quad (34)$$

obtained P becomes the re-tensile plastic zone's generated load $P_{RPG}$.

When the following load pair ($P_{min}$, $P_{max}$) is positioned between the minimum load $P_{min}$ and $P_{RPG}$, the load pair does not cause the initiation and growth of the crack. This load pair becomes the invalid load pair. In a case where a minimum load first gets out of this load space (D in FIG. 11), the equation (22) (wherein P is the next minimum load) and the equation (23) (wherein, $$L(\bar{x}_j)$$

is the inherent displacement occurring by the previous maximum load) are equalized and the crack opening displacement at the minimum load is obtained again on the conditions of the equations (31) and (32). In this case, it is necessary to reset the crack length of $c_b$ and the number of cycles by $\Delta N$. In a case where a maximum load first gets out of this load space, if the maximum load is larger than the past maximum load $P_{bmax}$, the processing goes ahead. When the maximum load is smaller than the past maximum load (C in FIG. 11), the processing goes ahead in a like manner, but the following special processing is carried out.

When the maximum load is smaller than the past maximum load, the equation (22) (wherein, P is the target maximum load) holds. Equalizing the equations (22) and (23) (wherein, $$L(\bar{x}_j)$$

is the inherent displacement occurring at the previous minimum load) and solving the equality equation on the conditions of the equations (31) and (32) can obtain the operating stress distribution. Obtained $\sigma(x_j)$ is substituted into the equation (22) to calculate the crack opening displacement $V(x)$ at the maximum load, and the inherent displacement $L(x)$ changes so as to be represented by the equation (6) in a position which has become the tensile plastic zone. In this case, as shown in FIG. 5, the position of an intersection point of a curve in a case where the inherent displacement $L(x)$ at the maximum load is elastically shrunk in accordance with the compressive yield and the crack opening displacement $V(x)$ at the maximum load becomes the tip position $\omega^+$ of the tensile plastic zone at the maximum load.

When the following load pair $(P_{min}, P_{max})$ is positioned between $P_{min}$ and $P_{RPG}$, the load pair does not cause the growth of the crack. This load pair becomes the invalid load pair. In a case where a minimum load first gets out of this load space (D in FIG. 11), the processing returns to the step S102 using this load and the crack opening displacement and the inherent displacement at the minimum load after the growth of the crack are obtained again. When a maximum load first gets out of this load space (C in FIG. 11), on the other hand, the processing goes ahead.

According to the method for estimating the fatigue crack growth curve according to the present invention having the configuration described above, it is possible to estimate the shape and the process of growth of the crack on a cycle basis in accordance with a practical phenomenon in which the crack continuously grows from an absent state. Thus, it is possible to precisely estimate fatigue life of metal and the detailed behavior of crack growth.

When the constant amplitude load continues for a while, the crack can be grown at a time with considering that the upper limit for the increment of the crack which can advance at a time by calculation is 5% of the fatigue damage accumulated region $\omega$, so that it is possible to omit time for calculation.

Furthermore, the re-tensile plastic zone's generated load and the re-compressive plastic zone's generated load are calculated, and only the load pair which contributes to the initiation and growth of the crack is extracted by using these values as threshold values. Therefore, the load which does not cause the occurrence of the tensile plastic zone and the compressive plastic zone at the crack tip is regarded as the load without growing the crack, so that it is possible to omit calculation for the crack growth.

Second Embodiment

In the first embodiment of the present invention, $S(x)$ and $s_{mR}(x)$ between divided points are assumed to be linearly changed by the first-order approximation. In the second embodiment of the present invention, the fatigue crack growth curve is estimated by using second-order approximation.

$S(x)$ and $s_{mR}(x)$ between the divided points are simplified as follows by the second-order approximation.

[Equation 39]

$$Sx_i = a_i x^2 + b_i x + c_i$$

$$S_{mR}x_i = a_{mRi} x^2 + b_{mRi} x + c_{mRi}$$

wherein,

-continued $$a_i = \frac{1}{x_{i+2} - x_{i+1}} \left( \frac{S_{i+2} - S_i}{x_{i+2} - x_i} - \frac{S_{i+1} - S_i}{x_{i+1} - x_i} \right)$$

$$b_i = \frac{S_{i+2} - S_i}{x_{i+2} - x_i} - \frac{x_{i+2} - x_i}{x_{i+2} - x_{i+1}} \left( \frac{S_{i+2} - S_i}{x_{i+2} - x_i} - \frac{S_{i+1} - S_i}{x_{i+1} - x_i} \right)$$

$$c_i = S_{i+2} - \frac{x_{i+2}^2}{x_{i+2} - x_{i+1}} \left( \frac{S_{i+2} - S_i}{x_{i+2} - x_i} - \frac{S_{i+1} - S_i}{x_{i+1} - x_i} \right) -$$

$$x_{i+2} \left\{ \frac{S_{i+2} - S_i}{x_{i+2} - x_i} - \frac{x_{i+2} - x_i}{x_{i+2} - x_{i+1}} \left( \frac{S_{i+2} - S_i}{x_{i+2} - x_i} - \frac{S_{i+1} - S_i}{x_{i+1} - x_i} \right) \right\}$$

(ditto for $S_{mR}(X)_i$)

Substituting equation (2) into equation (1),

[Equation 40]

$$P_{cmax} \sum_{i=1}^{n} \left[ a_i \left\{ \left( -x_i \sqrt{a^2 - x_i^2} + a^2 \sin^{-1} \frac{x_i}{a} \right) - \left( -x_{i-1} \sqrt{a^2 - x_{i-1}^2} + a^2 \sin^{-1} \frac{x_{i-1}}{a} \right) \right\} + b_i \sqrt{a^2 - x_{i-1}} - \sqrt{a^2 - x_i} + c_i \left( \sin^{-1} \frac{x_i}{a} - \sin^{-1} \frac{x_{i-1}}{a} \right) \right] + \sum_{i=1}^{n} \left[ a_{mRi} \left\{ \left( -x_i \sqrt{a^2 - x_i^2} + a^2 \sin^{-1} \frac{x_i}{a} \right) - \left( -x_{i-1} \sqrt{a^2 - x_{i-1}^2} + a^2 \sin^{-1} \frac{x_{i-1}}{a} \right) \right\} + b_{mRi} \left( \sqrt{a^2 - x_{i-1}} - \sqrt{a^2 - x_i} \right) + c_{mRi} \left( \sin^{-1} \frac{x_i}{a} - \sin^{-1} \frac{x_{i-1}}{a} \right) \right] = \frac{\pi \lambda \sigma_{cr}}{4a}$$

(3)' is obtained.

The tip position a of the tensile plastic zone is obtained from equation (3)'. The tip position $\omega^+$ of the tensile plastic zone in this cycle becomes a.

Thus, the crack opening displacement $V(x_j)$ at $x_j$ is represented as follows.

[Equation 41]

$$V(x_j) = P \sum_{i=1}^{n} \int_{x_{i-1}}^{x_i} (a_i x^2 + b_i x + c_i) F(x_j, x, a) dx + \sum_{i=1}^{n} \int_{x_{i-1}}^{x_i} (a_{mRi} x^2 + b_{mRi} x + c_{mRi}) F(x_j, x, a) dx - \lambda \sigma_{CY} \int_0^a F(x_j, x, a) dx$$

(4)'

As in the case of the first embodiment, it is possible to obtain the inherent displacement $L(x)$ at the maximum load by using equation (6) from the (factitious) crack opening displacement $V(x_j)$ obtained from the foregoing equations (4)' and (5).

The crack opening displacement in the unloading process, which is represented by equation (7) in the first embodiment, is represented as follows in the second embodiment.

[Equation 42]

$$V(x_j) = P \sum_{i=1}^{n} \int_{x_{i-1}}^{x_i} (a_i x^2 + b_i x + c_i) F(x_j, x, a) dx + \qquad (7)'$$
$$\sum_{i=1}^{n} \int_{x_{i-1}}^{x_i} (a_{mRi} x^2 + b_{mRi} x + c_{mRi}) F(x_j, x, a) dx +$$
$$\sum_{i=1}^{n} \int_{x_{i-1}}^{x_i} (a_{\sigma i} x^2 + b_{\sigma i} x + c_{\sigma i}) F(x_j, x, a) dx$$

wherein, as with $S(x)$ and $s_{mR}(x)$, $a_{\sigma i}$, $b_{\sigma i}$, and $c_{\sigma i}$ are coefficients in the case of simplifying stress applied to a rod element between the divided points by the second-order approximation. Calculation is carried out with substituting equation (7)' for equation (7) in the first embodiment as described below.

In the second embodiment, the following equations (22)' and (24)' are substituted for equations (22) and (24) respectively, which represent the crack opening displacement V' in the case of reaching the minimum load without propagating the crack and the crack opening displacement V" at the minimum load in a case where the crack propagates by $\Delta c$ without forming the crack closing zone, which are schematically shown in FIG. 10.

[Equation 43]

$$V(\bar{x}_j) = P \sum_{i=1}^{n} \int_{x_{i-1}}^{x_i} (a_i x^2 + b_i x + c_i) F(\bar{x}_j, x, a) dx + \qquad (22)'$$
$$\sum_{i=1}^{n} \int_{x_{i-1}}^{x_i} (a_{mRi} x^2 + b_{mRi} x + c_{mRi}) F(\bar{x}_j, x, a) dx +$$
$$\sum_{i=0}^{k} \delta(i) \sigma_i \left\{ \zeta(i) \int_{x_{i-1}}^{x_i} \frac{x - x_{i-1}}{x_i - x_{i-1}} F(\bar{x}_j, x, a) dx - \xi(i) \int_{x_i}^{x_{i+1}} \frac{x - x_{i+1}}{x_{i+1} - x_i} F(\bar{x}_j, x, a) dx \right\} +$$
$$\sum_{i=k+1}^{l+1} \sigma_i \left\{ \zeta(i) \int_{x-1}^{x_i} \frac{x - x_{i-1}}{x_i - x_{i-1}} F(\bar{x}_j, x, a) dx - \xi(i) \int_{x_i}^{x_{i+1}} \frac{x - x_{i+1}}{x_{i+1} - x_i} F(\bar{x}_j, x, a) dx \right\} +$$
$$\sum_{i=l+1}^{n} \sigma_{i+1} \left\{ \zeta(i) \int_{x_{i-1}}^{x_i} \frac{x - x_{i-1}}{x_i - x_{i-1}} F(\bar{x}_j, x, a) dx - \xi(i) \int_{x_i}^{x_{i+1}} \frac{x - x_{i+1}}{x_{i+1} - x_i} F(\bar{x}_j, x, a) dx \right\}$$

-continued

[Equation 44]

$$V(\bar{x}_j) = P_{max} \sum_{i=1}^{n} \int_{x_{i-1}}^{x_i} (a_i x^2 + b_i x + c_i) F(\bar{x}_j, x, a) dx + \qquad (24)'$$
$$\sum_{i=1}^{n} \int_{x_{i-1}}^{x_i} (a_{mRi} x^2 + b_{mRi} x + c_{mRi}) F(\bar{x}_j, x, a) dx +$$
$$\sum_{i=0}^{k} \delta(i) \sigma_i \left\{ \zeta(i) \int_{x_{i-1}}^{x_i} \frac{x - x_{i-1}}{x_i - x_{i-1}} F(\bar{x}_j, x, a) dx - \xi(i) \int_{x_i}^{x_{i+1}} \frac{x - x_{i+1}}{x_{i+1} - x_i} F(\bar{x}_j, x, a) dx \right\} +$$
$$\sum_{i=l+1}^{n} \sigma_{i+1} \left\{ \zeta(i) \int_{x_{i-1}}^{x_i} \frac{x - x_{i-1}}{x_i - x_{i-1}} F(\bar{x}_j, x, a) dx - \xi(i) \int_{x_i}^{x_{i+1}} \frac{x - x_{i+1}}{x_{i+1} - x_i} F(\bar{x}_j, x, a) dx \right\}$$

The following equation (29)' is also substituted for equation (29) which represent the crack opening displacement V in a case where the tip position a of the tensile plastic zone is far away beyond the past tip position a' of the tensile plastic zone.

[Equation 45]

$$V(\bar{x}_j) = P \sum_{i=1}^{n} \int_{x_{i-1}}^{x_i} (a_i x^2 + b_i x + c_i) F(\bar{x}_j, x, a) dx + \qquad (29)'$$
$$\sum_{i=1}^{n} \int_{x_{i-1}}^{x_i} (a_{mRi} x^2 + b_{mRi} x + c_{mRi}) F(\bar{x}_j, x, a) dx -$$
$$\lambda \sigma_Y \sum_{i=1}^{k} \int_{x_{i-1}}^{x_i} (\delta(i) - \delta(i-1)) F(x_j, x, \bar{a}) dx -$$
$$\lambda \sigma_Y \int_{c}^{a} F(\bar{x}_j, x, a) dx$$

The fatigue crack growth curve is estimated by carrying out calculation after that in a like manner as the first embodiment.

Using the second-order approximation on $S(x)$ and $s_{mR}(x)$ between the divided points, as described above, makes it possible to further precisely estimate the fatigue crack growth curve than the case of using the first-order approximation.

INDUSTRIAL APPLICABILITY

The present invention can precisely estimate fatigue life of metal and the detailed behavior of the initiation and growth of a crack in accordance with a practical phenomenon in which the crack continuously grows from a size of zero, in other words, from an absent state in a sound area. Thus, it is possible to quantitatively forecast the fatigue life of a new structure from the designing stage in order to extremely highly contribute to the prevention of a fatigue accident of the structure. Also the remaining life of an existing structure is precisely and quantitatively assessed, so that it is possible to create a rational maintenance plan and greatly reduce excessive maintenance cost, which was necessary so far. Therefore, the present invention is usable for estimating the life of equipment and structures (for example, a highway structure, a ship, an electric power generation plant, a bridge, a steel tower, an automobile, an airplane, earthmoving equipment, steelmaking equipment, and the like) of every description.

The invention claimed is:

1. A method for estimating a fatigue crack growth curve from a sound area using equivalent distributed stress which reproduces a relation between a crack length and a stress intensity factor in an actual structure by external force and internal force due to residual stress into a straight crack in an infinitely wide plate, the method comprising:

a first step of calculating a tip position of a tensile plastic zone and an inherent displacement which forms a tensile residual deformation layer at a maximum load during cyclic loading on a stress concentrated area;

a second step of calculating the inherent displacement at a minimum load of the cyclic load, and calculating a tip position of a compressive plastic zone from the inherent displacement;

a third step of calculating a fatigue damage accumulated region formed ahead of the crack from the tip position of the tensile plastic zone and the tip position of the compressive plastic zone, and calculating an increment of the crack from the fatigue damage accumulated region to add the increment of the crack to the crack length;

a fourth step of setting, when the crack length from the sound area is smaller than a first grain size at a notch root, an increment of plastic strain to "0", the plastic strain being formed by a pair of the maximum load and the minimum load in applying the cyclic load inside the grain only in the compressive plastic zone in a load cycle in which the tensile plastic zone at the maximum load is larger than the compressive plastic zone at the minimum load, or only in the tensile plastic zone in a load cycle in which the tensile plastic zone at the maximum load is smaller than the compressive plastic zone at the minimum load, then calculating an increment of plastic strain outside of the grain to calculate cumulative plastic strain from the increment of plastic strain, and, when the crack length from the sound area is equal to or larger than the first grain size at the notch root, calculating the increment of plastic strain and calculating the cumulative plastic strain from the increment of plastic strain, and, when the cumulative plastic strain inside the grain reaches a ductility limit specific to a material composing the stress concentrated area, judging the crack to have changed into an opening mode crack, and calculating the inherent displacement taken in a crack incremental region; and a fifth step of calculating a yield stress under the next cyclic load at the next maximum load, and returning the process to the first step.

2. The method for estimating a fatigue crack growth curve according to claim 1, wherein, when a constant amplitude load is repeatedly and continuously applied on the stress concentrated area, in the third step, the fatigue damage accumulated region is calculated in the third step, the fatigue damage accumulated region provides an increment of the crack which can propagate at a time, and the number of cycles necessary for the increment of the crack is calculated from a crack propagation equation, and in the fourth step, when the crack length from the sound area is smaller than the diameter of the first grain at the notch root, the increment of plastic strain is set to "0,"

outside of the grain, the increment of plastic strain is calculated from the variation of the inherent displacement, and the cumulative plastic strain is calculated by multiplying the increment of plastic strain by the number of cycles, and, when the crack length from the sound area is equal to or larger than the first grain size at the notch root, the increment of plastic strain is calculated from the variation of the inherent displacement, and the cumulative plastic strain is calculated by multiplying the increment of plastic strain by the number of cycles, and inside the grain, when the cumulative plastic strain reaches the ductility limit specific to the material composing the stress concentrated area, the crack is judged to have changed into the opening crack, and the crack mode index is set to "0," and outside of the grain, the inherent displacement taken in the crack incremental region is calculated from the cumulative plastic strain and the yield stress and the plastic constraint factor under the cyclic load.

3. The method for estimating a fatigue crack growth curve according to claim 2, further comprising a load extraction step of extracting only a load pair of a maximum load and a minimum load contributing to crack growth.

4. The method for estimating a fatigue crack growth curve according to claim 1, further comprising a load extraction step of extracting only a load pair of a maximum load and a minimum load contributing to crack growth.

5. The method for estimating a fatigue crack growth curve according to claim 4, wherein in the load extraction step the load pair of the maximum load and the minimum load contributing to the crack growth is extracted with the use of a re-compressive plastic zone's generated load calculated from the inherent displacement, the vertically equivalent distributed stress applied on the x axis when a unit load is applied, the vertical equivalent distributed stress in the x axis caused by the static load, the equivalent distributed stress corresponding to the residual stress applied on the x axis, the yield stress under the cyclic load, and the plastic constraint factor at the maximum load in an unloading process in continuously applying the cyclic load on the stress concentrated area, and a re-tensile plastic zone's generated load calculated from the inherent displacement, the vertically equivalent distributed stress when a unit external load is applied, the vertical equivalent distributed stress in the x axis caused by the static load, the equivalent distributed stress corresponding to the residual stress applied on the x axis, the yield stress under the cyclic load, and the plastic constraint factor at the minimum load in a loading process in continuously applying the cyclic load on the stress concentrated area, as threshold values.

6. A method for estimating a fatigue crack growth curve from a sound area using equivalent distributed stress which reproduces a relation between a crack length and a stress intensity factor in an actual structure by external force and internal force due to residual stress into a straight crack in an infinitely wide plate, the method comprising:

a first step of setting an initial value of the crack length to "0", and setting an initial value of a crack mode index to "1", which represents a shear mode crack and an opening mode crack by "1" or "0" and then calculating, when a cyclic load is applied on a stress concentrated area, an inherent displacement which forms a tensile residual deformation layer at a maximum load from a tip position of a tensile plastic zone which is calculated from vertical equivalent distributed stress applied on an arbitrary x axis at the maximum load, vertical equivalent distributed stress in the x axis caused by a static load, equivalent distributed stress corresponding to residual stress applied on the x axis, and a yield stress and a plastic constraint factor under the cyclic load;

a second step of calculating the inherent displacement at a minimum load from the vertical equivalent distributed stress applied on the x axis in the case of applying the minimum load and a unit external load of the cyclic load, the vertical equivalent distributed stress in the x axis caused by the static load, the equivalent distributed stress corresponding to the residual stress applied on the x axis, and the inherent displacement at the maximum load, and then calculating a tip position of a compressive plastic zone at the minimum load from the inherent displacement at the maximum load and n inherent displacement at the minimum load, and calculating the inherent displacement in a compressive yield zone from the inherent displacement at the minimum load and the yield stress and the plastic constraint factor under the cyclic load;

a third step of calculating a fatigue damage accumulated region formed ahead of the crack from the tip position of the tensile plastic zone and the tip position of the compressive plastic zone, and calculating an increment of the crack from the fatigue damage accumulated region in order to add the increment of the crack to the crack length;

a fourth step of setting, when the crack length from the sound area is smaller than a first grain size at a notch root, an increment of plastic strain to "0", the plastic strain being formed by a pair of the maximum load and the minimum load in applying the cyclic load inside the grain only in the compressive plastic zone in a load cycle in which the tensile plastic zone at the maximum load is larger than the compressive plastic zone at the minimum load, or only in the tensile plastic zone in a load cycle in which the tensile plastic zone at the maximum load is smaller than the compressive plastic zone at the minimum load, then calculating an increment of plastic strain outside of the grain from the variation of the inherent displacement to calculate cumulative plastic strain from the increment of plastic strain, and, when the crack length from the sound area is equal to or larger than the first grain size at the notch root, calculating the increment of plastic strain from the variation of the inherent displacement, and calculating the cumulative plastic strain from the increment of plastic strain, and, when the cumulative plastic strain inside the grain reaches a ductility limit specific to a material composing the stress concentrated area, judging the crack to have changed into an opening mode crack, and setting the crack mode index to "0", and calculating the inherent displacement taken in a crack incremental region and the yield stress and the plastic constraint factor under the cyclic load; and a fifth step of calculating a yield stress under the next cyclic load at the next maximum load from the vertical equivalent distributed stress applied on the arbitrary x axis at the next maximum load, the vertical equivalent distributed stress in the x axis caused by the static load, the equivalent distributed stress corresponding to the residual stress applied on the x axis, and the plastic constraint factor, and returning the process to the first step.

7. The method for estimating a fatigue crack growth curve according to claim 6, wherein, when a constant amplitude load is repeatedly and continuously applied on the stress concentrated area, in the third step, the fatigue damage accumulated region is calculated in the third step, the fatigue damage accumulated region provides an increment of the crack which can propagate at a time, and the number of cycles necessary for the increment of the crack is calculated from a crack propagation equation, and in the fourth step, when the crack length from the sound area is smaller than the diameter of the first grain at the notch root, the increment of plastic strain is set to "0,"

outside of the grain, the increment of plastic strain is calculated from the variation of the inherent displacement, and the cumulative plastic strain is calculated by multiplying the increment of plastic strain by the number of cycles, and, when the crack length from the sound area is equal to or larger than the first grain size at the notch root, the increment of plastic strain is calculated from the variation of the inherent displacement, and the cumulative plastic strain is calculated by multiplying the increment of plastic strain by the number of cycles, and inside the grain, when the cumulative plastic strain reaches the ductility limit specific to the material composing the stress concentrated area, the crack is judged to have changed into the opening crack, and the crack mode index is set to "0," and outside of the grain, the inherent displacement taken in the crack incremental region is calculated from the cumulative plastic strain and the yield stress and the plastic constraint factor under the cyclic load.

8. The method for estimating a fatigue crack growth curve according to claim 6, further comprising a load extraction step of extracting only a load pair of a maximum load and a minimum load contributing to crack growth.

9. A computer readable medium having stored thereon an estimation program of a fatigue crack growth curve for making a computer, which sets an initial crack length to "0" and sets an initial value of a crack mode index to "1" which represents a shear mode crack and an opening mode crack by "1" or "0", perform a method comprising:

a first step of calculating, when a cyclic load is applied on a stress concentrated area, an inherent displacement which forms a tensile residual deformation layer at a maximum load from a tip position of a tensile plastic zone which is calculated from vertical equivalent distributed stress applied on an arbitrary x axis at the maximum load, vertical equivalent distributed stress in the x axis caused by a static load, equivalent distributed stress corresponding to residual stress applied on axis, and a yield stress and a plastic constraint factor under the cyclic load, and storing the tip position of the tensile plastic zone and the inherent displacement in a memory;

a second step of calculating a inherent displacement at a minimum load from the vertical equivalent distributed stress applied on the x axis in the case of applying the minimum load and a unit external load of the cyclic load, the vertical equivalent distributed stress in the x axis caused by the static load, the equivalent distributed stress corresponding to the residual stress applied on the x axis, and the inherent displacement at the maximum load read from the memory, and then calculating a tip position of a compressive plastic zone at the minimum load from the inherent displacement at the maximum load read from the memory, and the thickness distribution of the tensile residual deformation layer at the minimum load, and calculating the inherent displacement in a compressive yield zone from the inherent displacement at the minimum load and the yield stress and the plastic constraint factor under the cyclic load, and storing the inherent displacement and the tip position of the compressive plastic zone in the memory;

a third step of calculating a fatigue damage accumulated region formed ahead of the crack from the tip position of the tensile plastic zone and the tip position of the compressive plastic zone which are read from the memory, and calculating an increment of the crack from the fatigue damage accumulated region in order to add the increment of the crack to the crack length and store a result in the memory;

a fourth step of setting, when the crack length from the sound area is smaller than a first grain size at a notch root, an increment of plastic strain to "0", the plastic strain being formed by a pair of the maximum load and the minimum load in applying the cyclic load inside the grain only in the compressive plastic zone in a load cycle in which the tensile plastic zone at the maximum load is larger than the compressive plastic zone at the minimum load, or only in the tensile plastic zone in a load cycle in which the tensile plastic zone at the maximum load is smaller than the compressive plastic zone at the minimum load, then calculating an increment of plastic strain outside of the grain from the variation of the inherent displacement read from the memory, in order to calculate cumulative plastic strain from the increment of plastic strain and store it in the memory, and, when the crack length from the sound area is equal to or larger than the first grain size at the notch root, calculating the increment of plastic strain from the variation of the inherent displacement read from the memory, and calculating the cumulative plastic strain from the increment of plastic strain to store it in the memory, and, when the cumulative plastic strain inside the grain reaches a ductility limit specific to a material composing the stress concentrated area, judging the crack to have changed into an opening mode crack, and setting the crack mode index to "0" to store it in the memory, and calculating the inherent displacement taken in a crack incremental region and the yield stress and the plastic constraint factor under the cyclic load to store it in the memory; and a fifth step of calculating a yield stress under the next cyclic load at the next maximum load from the vertical equivalent distributed stress applied on the arbitrary x axis at the next maximum load, the vertical equivalent distributed stress in the x axis caused by the static load, the equivalent distributed stress corresponding to the residual stress applied on the x axis, the plastic constraint factor, and the crack mode index read from the memory, and storing it in the memory, and then returning the process to the first step.

10. An estimation device of a fatigue crack growth curve comprising:

memory means for storing an initial value of a crack length set to "0" and an initial value of a crack mode index to "1", which represents a shear mode crack and an opening mode crack by "1" or "0";

first operation means for calculating, when a cyclic load is applied on a stress concentrated area, an inherent displacement which forms a tensile residual deformation layer at a maximum load from a tip position of a tensile plastic zone which is calculated from vertical equivalent distributed stress applied on an arbitrary x axis at the maximum load, vertical equivalent distributed stress in the x axis caused by a static load, equivalent distributed stress corresponding to residual stress applied on the x axis, and a yield stress and a plastic constraint factor under the cyclic load, and storing the tip position of the tensile plastic zone and the inherent displacement in the memory means;

second operation means for calculating a inherent displacement at a minimum load from the vertical equivalent distributed stress applied on the x axis in the case of applying the minimum load and a unit external load of the cyclic load, the vertical equivalent distributed stress in the x axis caused by the static load, the equivalent distributed stress corresponding to the residual stress applied on the x axis, and the inherent displacement at the maximum load read from the memory means, and then calculating a tip position of a compressive plastic zone at the minimum load from the inherent displacement at the maximum load read from the memory means and the inherent displacement at the minimum load, and calculating the inherent displacement in a compressive yield zone from the inherent displacement at the minimum load and the yield stress and the plastic constraint factor under the cyclic load, and storing the inherent displacement and the tip position of the compressive plastic zone in the memory means;

third operation means for calculating a fatigue damage accumulated region formed ahead of the crack from the tip position of the tensile plastic zone and the tip position of the compressive plastic zone which are read from the memory means, and calculating an increment of the crack from the fatigue damage accumulated region in order to add the increment of the crack to the crack length and store a result in the memory means;

fourth operation means for setting, when the crack length from the sound area is smaller than a first grain size at a notch root, an increment of plastic strain to "0", the plastic strain being formed by a pair of the maximum load and the minimum load in applying the cyclic load inside the grain only in the compressive plastic zone in a load cycle in which the tensile plastic zone at the maximum load is larger than the compressive plastic zone at the minimum load, or only in the tensile plastic zone in a load cycle in which the tensile plastic zone at the maximum load is smaller than the compressive plastic zone at the minimum load, then calculating an increment of plastic strain outside of the grain from the variation of the inherent displacement read from the memory means in order to calculate cumulative plastic strain from the increment of plastic strain and store it in the memory means, and, when the crack length from the sound area is equal to or larger than the first grain size at the notch root, calculating the increment of plastic strain from the variation of the inherent displacement read from the memory means, and calculating the cumulative plastic strain from the increment of plastic strain to store it in the memory means, and, when the cumulative plastic strain inside the grain reaches a ductility limit specific to a material composing the stress concentrated area, judging the crack to have changed into an opening mode crack, and setting the crack mode index to "0" to store it in the memory means, and calculating the inherent displacement taken in a crack incremental region and the yield stress and the plastic constraint factor under the cyclic load to store it in the memory means; and fifth operation means for calculating a yield stress under the next cyclic load at the next maximum load from the vertical equivalent distributed stress applied on the arbitrary x axis at the next maximum load, the vertical equivalent distributed stress in the x axis caused by the static load, the equivalent distributed stress corresponding to the residual stress applied on the x axis, the plastic constraint factor, and the crack mode index read from the memory means, and storing it in the memory means, and then returning the process to the first operation means.

* * * * *